US012629062B2

(12) United States Patent
　　Katnani et al.

(10) Patent No.:　US 12,629,062 B2
(45) **Date of Patent:　*May 19, 2026**

(54) TIME DOMAIN-BASED OPTICAL MEASUREMENT SYSTEMS AND METHODS CONFIGURED TO MEASURE ABSOLUTE PROPERTIES OF TISSUE

(71) Applicant: HI LLC, Culver City, CA (US)

(72) Inventors: Husam Katnani, Braintree, MA (US); Katherine Perdue, Los Angeles, CA (US); Ryan Field, Culver City, CA (US); Isai Olvera, South Portland, ME (US)

(73) Assignee: HI LLC, Culver City, CA (US)

( * ) Notice: Subject to any disclaimer, the term of this patent is extended or adjusted under 35 U.S.C. 154(b) by 72 days.

This patent is subject to a terminal disclaimer.

(21) Appl. No.: 18/671,696

(22) Filed: May 22, 2024

(65) Prior Publication Data

US 2024/0306958 A1　　Sep. 19, 2024

Related U.S. Application Data

(63) Continuation of application No. 17/176,560, filed on Feb. 16, 2021, now Pat. No. 12,029,558.

(Continued)

(51) Int. Cl.
　　*A61B 5/1455*　　(2006.01)
　　*A61B 5/00*　　(2006.01)
　　(Continued)

(52) U.S. Cl.
　　CPC ........ *A61B 5/14553* (2013.01); *A61B 5/6803* (2013.01); *A61B 5/4088* (2013.01);
　　(Continued)

(58) Field of Classification Search
　　CPC . A61B 5/14553; A61B 5/6803; A61B 5/4088; A61B 2090/306;
　　(Continued)

(56) References Cited

U.S. PATENT DOCUMENTS 5,853,370 A　　12/1998　Chance et al.
6,240,309 B1　　5/2001　Yamashita et al.
(Continued)

FOREIGN PATENT DOCUMENTS

WO　　2005050156 A2　　6/2005
WO　　2006041997 A2　　4/2006
WO　　2007048039 A2　　4/2007

OTHER PUBLICATIONS

Alayed, et al., Characterization of a Time-Resolved Diffuse Optical Spectroscopy Prototype Using Low-Cost, Compact Single Photon Avalanche Detectors for Tissue Optics Applications, Sensors 2018, 18, 3680; doi:10.3390/s18113680, Oct. 29, 2018.
(Continued)

*Primary Examiner* — Abid A Mustansir
(74) *Attorney, Agent, or Firm* — ALG Intellectual Property, LLC

(57)　　　ABSTRACT

An optical measurement system includes a detector configured to detect signal photons included in a light pulse after the signal photons enter a body of a user and are scattered by a target within the body and reference photons included in the light pulse, the reference photons being diverted to the detector without entering the body. The optical measurement system further includes a processing unit configured to determine a temporal distribution of the signal photons detected by the detector, determine a temporal distribution of the reference photons detected by the detector, and
(Continued)

generate measurement data based on the temporal distribution of the signal photons and the temporal distribution of the reference photons.

21 Claims, 28 Drawing Sheets

Related U.S. Application Data

(60) Provisional application No. 63/064,688, filed on Aug. 12, 2020, provisional application No. 63/012,538, filed on Apr. 20, 2020, provisional application No. 62/979,866, filed on Feb. 21, 2020.

(51) Int. Cl.
| | |
|---|---|
| *A61B 90/00* | (2016.01) |
| *A61B 90/30* | (2016.01) |

(52) U.S. Cl.
CPC . *A61B 2090/306* (2016.02); *A61B 2090/3614* (2016.02); *A61B 2562/0238* (2013.01)

(58) Field of Classification Search
CPC .... A61B 2090/3614; A61B 2562/0238; A61B 5/0086; A61B 2562/0233; A61B 2562/043; A61B 5/0002; A61B 5/0084; A61B 5/14552; A61B 5/686; A61B 5/6868; A61B 5/7275
See application file for complete search history.

(56) References Cited

U.S. PATENT DOCUMENTS

| | | | |
|---|---|---|---|
| 6,384,663 | B2 | 5/2002 | Cova et al. |
| 6,640,133 | B2 | 10/2003 | Yamashita et al. |
| 6,683,294 | B1 | 1/2004 | Herbert et al. |
| 7,356,365 | B2 | 4/2008 | Schurman |
| 7,547,872 | B2 | 6/2009 | Niclass et al. |
| 7,774,047 | B2 | 8/2010 | Yamashita et al. |
| 8,026,471 | B2 | 9/2011 | Itzler |
| 8,078,250 | B2 | 12/2011 | Chen et al. |
| 8,082,015 | B2 | 12/2011 | Yodh et al. |
| 8,518,029 | B2 | 8/2013 | Birmingham et al. |
| 8,633,431 | B2 | 1/2014 | Kim |
| 8,817,257 | B2 | 8/2014 | Herve |
| 9,058,081 | B2 | 6/2015 | Baxter |
| 9,076,707 | B2 | 7/2015 | Harmon |
| 9,131,861 | B2 | 9/2015 | Ince et al. |
| 9,316,735 | B2 | 4/2016 | Baxter |
| 9,401,448 | B2 | 7/2016 | Bienfang et al. |
| 9,419,635 | B2 | 8/2016 | Kumar et al. |
| 9,442,201 | B2 | 9/2016 | Schmand et al. |
| 9,529,079 | B1 | 12/2016 | Droz et al. |
| 9,574,936 | B2 | 2/2017 | Heinonen |
| 9,946,344 | B2 | 4/2018 | Ayaz et al. |
| D817,553 | S | 5/2018 | Aaskov et al. |
| D825,112 | S | 8/2018 | Saez |
| 10,158,038 | B1 | 12/2018 | Do et al. |
| 10,340,408 | B1 | 7/2019 | Katnani et al. |
| 10,424,683 | B1 | 9/2019 | Valle et al. |
| 10,515,993 | B2 | 12/2019 | Field et al. |
| 10,695,167 | B2 | 6/2020 | Van Heugten et al. |
| 10,697,829 | B2 | 6/2020 | Delic |
| 10,772,561 | B2 | 9/2020 | Donaldson |
| 10,809,796 | B2 | 10/2020 | Armstrong-Muntner et al. |
| 10,912,504 | B2 | 2/2021 | Nakaji et al. |
| 11,006,876 | B2 | 5/2021 | Johnson et al. |
| 11,006,878 | B2 | 5/2021 | Johnson et al. |
| 11,857,348 | B2 | 1/2024 | Field et al. |
| 11,903,676 | B2 | 2/2024 | Sorgenfrei et al. |
| 11,950,879 | B2 | 4/2024 | Field et al. |
| 2007/0083097 | A1 | 4/2007 | Fujiwara et al. |
| 2009/0012402 | A1 | 1/2009 | Mintz et al. |
| 2009/0054789 | A1 | 2/2009 | Kiguchi et al. |
| 2010/0249557 | A1 | 9/2010 | Besko et al. |
| 2011/0208675 | A1 | 8/2011 | Shoureshi et al. |
| 2013/0342835 | A1 | 12/2013 | Blacksberg |
| 2014/0046152 | A1 | 2/2014 | Bechtel et al. |
| 2014/0191115 | A1 | 7/2014 | Webster et al. |
| 2014/0217264 | A1 | 8/2014 | Shepard et al. |
| 2014/0275891 | A1 | 9/2014 | Muehlemann et al. |
| 2015/0038811 | A1 | 2/2015 | Asaka et al. |
| 2015/0041625 | A1 | 2/2015 | Dutton et al. |
| 2015/0054111 | A1 | 2/2015 | Niclass et al. |
| 2015/0077279 | A1 | 3/2015 | Song et al. |
| 2015/0150505 | A1 | 6/2015 | Kaskoun et al. |
| 2015/0327777 | A1 | 11/2015 | Kostic et al. |
| 2015/0364635 | A1 | 12/2015 | Bodlovic et al. |
| 2017/0030769 | A1 | 2/2017 | Clemens et al. |
| 2017/0031009 | A1 | 2/2017 | Davidovic et al. |
| 2017/0052065 | A1 | 2/2017 | Sharma et al. |
| 2017/0176596 | A1 | 6/2017 | Shpunt et al. |
| 2017/0179173 | A1 | 6/2017 | Mandai et al. |
| 2017/0202518 | A1 | 7/2017 | Furman et al. |
| 2017/0281086 | A1 | 10/2017 | Donaldson |
| 2017/0343384 | A1 | 11/2017 | Nakazato et al. |
| 2017/0363467 | A1 | 12/2017 | Clemens et al. |
| 2017/0367650 | A1 | 12/2017 | Wallois et al. |
| 2018/0014741 | A1 | 1/2018 | Chou |
| 2018/0027196 | A1 | 1/2018 | Yang et al. |
| 2018/0033751 | A1 | 2/2018 | Ban et al. |
| 2018/0039053 | A1 | 2/2018 | Kremer et al. |
| 2018/0070830 | A1 | 3/2018 | Sutin et al. |
| 2018/0070831 | A1 | 3/2018 | Sutin et al. |
| 2018/0089848 | A1 | 3/2018 | Yang et al. |
| 2019/0113385 | A1 | 4/2019 | Fukuchi |
| 2019/0175068 | A1 | 6/2019 | Everdell |
| 2019/0355861 | A1 | 11/2019 | Katnani et al. |
| 2019/0363210 | A1 | 11/2019 | Valle et al. |
| 2019/0388018 | A1 | 12/2019 | Horstmeyer et al. |
| 2020/0044098 | A1 | 2/2020 | Azuma et al. |
| 2020/0060542 | A1 | 2/2020 | Alford et al. |
| 2020/0116838 | A1 | 4/2020 | Erdogan et al. |
| 2020/0196932 | A1 | 6/2020 | Johnson et al. |
| 2020/0253479 | A1 | 8/2020 | Nurmikko |
| 2020/0315510 | A1 | 10/2020 | Johnson et al. |
| 2020/0337624 | A1 | 10/2020 | Johnson et al. |
| 2020/0390358 | A1 | 12/2020 | Johnson et al. |
| 2021/0290066 | A1 | 9/2021 | Field et al. |

OTHER PUBLICATIONS

Ban, et al., Kernel Flow: a high channel count scalable TD-fNIRS system, https://www.spiedigitallibrary.org/conference-proceedings-of-spie Proc. of SPIE vol. 11663, 116630B doi: 10.1117/12.2582888, Mar. 5, 2021.

Ban, et al., Kernel Flow: a high channel count scalable time-domain functional near-infrared spectroscopy system, https://www.spiedigitallibrary.org/journals/Journal-of-Biomedical-Optics on Jan. 18, 2022.

Contini, et al., Photon migration through a turbid slab described by a model based on diffusion approximation. I. Theory, Appl. Opt. 36(19), 4587 (1997).

Di Sieno, et al., Probe-hosted large area silicon photomultiplier and high-throughput timing electronics for enhanced performance time-domain functional near-infrared spectroscopy, Biomed. Opt. Express 11(11), 6389 (2020).

Fishburn, et al., Temporal Derivative Distribution Repair (TDDR): A motion correction method for fNIRS, Neuroimage. Jan. 1, 2019; 184: 171-179. doi:10.1016/j.neuroimage.2018.09.025.

Huppert, et al., HomER: a review of time-series analysis methods for near-infrared spectroscopy of the brain, Appl. Opt. 48(10), D280 (2009).

Kienle, et al., Improved solutions of the steady-state and the time-resolved diffusion equations for reflectance from a semi-infinite turbid medium, J. Opt. Soc. Am. A 14(1), 246 (1997).

Konugolu, et al., Broadband (600-1350 nm) Time-Resolved Diffuse Optical Spectrometer for Clinical Use, IEEE Journal of Selected Topics in Quantum Electronics, vol. 22, No. 3, May/Jun. 2016.

(56)         References Cited

OTHER PUBLICATIONS

Lacerenza, et al., Wearable and wireless time-domain near-infrared spectroscopy system for brain and muscle hemodynamic monitoring, Biomed. Opt. Express 11(10), 5934 (2020).

Lange, et al., Clinical Brain Monitoring with Time Domain NIRS: A Review and Future Perspectives, Applied Sciences 9(8), 1612 (2019).

Lange, et al., MAESTROS: A Multiwavelength Time-Domain NIRS System to Monitor Changes in Oxygenation and Oxidation State of Cytochrome-C-Oxidase, IEEE J. Select. Topics Quantum Electron. 25(1), 1-12 (2019).

Martelli, et al., Optimal estimation reconstruction of the optical properties of a two-layered tissue phantom from time-resolved single-distance measurements, Journal of Biomedical Optics 20(11), 115001 (Nov. 2015).

Mora, et al., Fast silicon photomultiplier improves signal harvesting and reduces complexity in time-domain diffuse optics, Opt. Express 23(11), 13937 (2015).

Pifferi, et al., Performance assessment of photon migration instruments: the MEDPHOT protocol, Applied Optics, 44 (11), 2104-2114, 2005.

Prahl, Optical Absorption of Hemoglobin, http://omlc.ogi.edu/spectra/hemoglobin/index.html, 1999.

Re, et al., Multi-channel medical device for time domain functional near infrared spectroscopy based on wavelength space multiplexing, Biomed. Opt. Express 4(10), 2231 (2013).

Renna, et al., Eight-Wavelength, Dual Detection Channel Instrument for Near-Infrared Time-Resolved Diffuse Optical Spectroscopy, IEEE J. Select. Topics Quantum Electron. 25(1), 1-11 (2019).

Torricelli, et al., Time domain functional NIRS imaging for human brain mapping, NeuroImage 85, 28-50 (2014).

Wabnitz, et al., Depth-selective data analysis for time-domain fNIRS: moments vs. time windows, Biomed. Opt. Express 11(8), 4224 (2020).

Wabnitz, et al., Performance assessment of time-domain optical brain imagers, part 1: basic instrumental performance protocol, Journal of Biomedical Optics 19(8), 086010 (Aug. 2014).

Wabnitz, et al., Performance assessment of time-domain optical brain imagers, part 2: nEUROPt protocol, Journal of Biomedical Optics 19(8), 086012 (Aug. 2014).

Wojtkiewicz, et al., Self-calibrating time-resolved near infrared spectroscopy, Biomed. Opt. Express 10(5), 2657 (2019).

Zucchelli, et al., Method for the discrimination of superficial and deep absorption variations by time domain fNIRS, 2013 OSA Dec. 1, 2013 | vol. 4, No. 12 | DOI:10.1364/BOE.4.002893 | Biomedical Optics Express 2893, 2013.

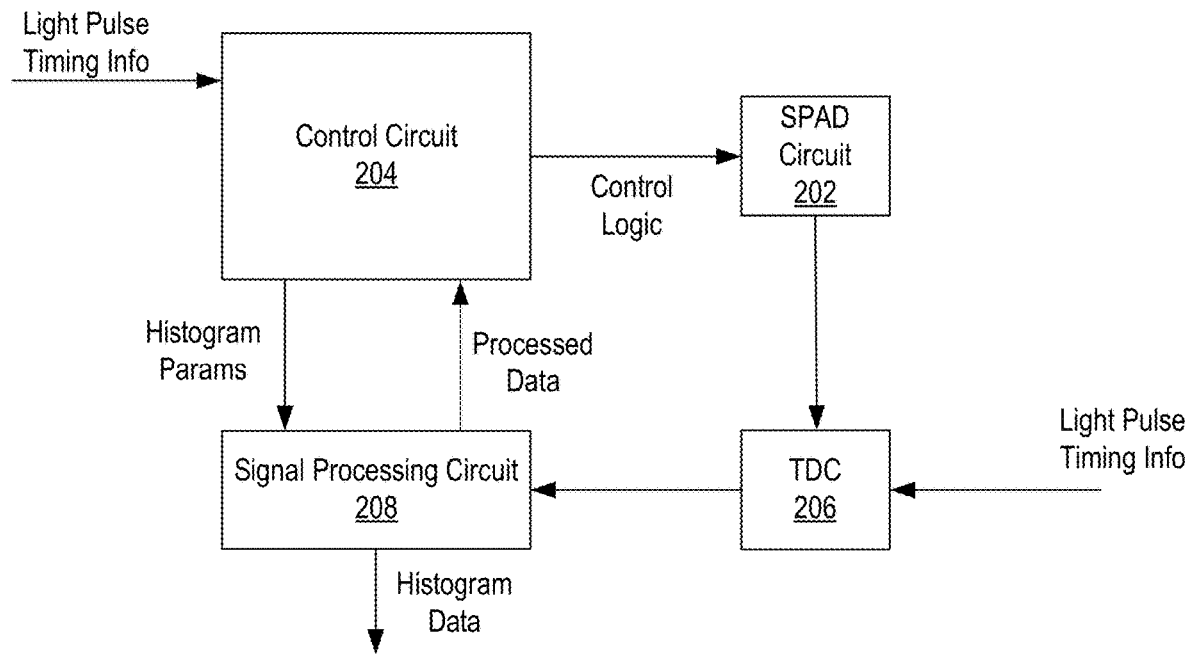
Fig. 2

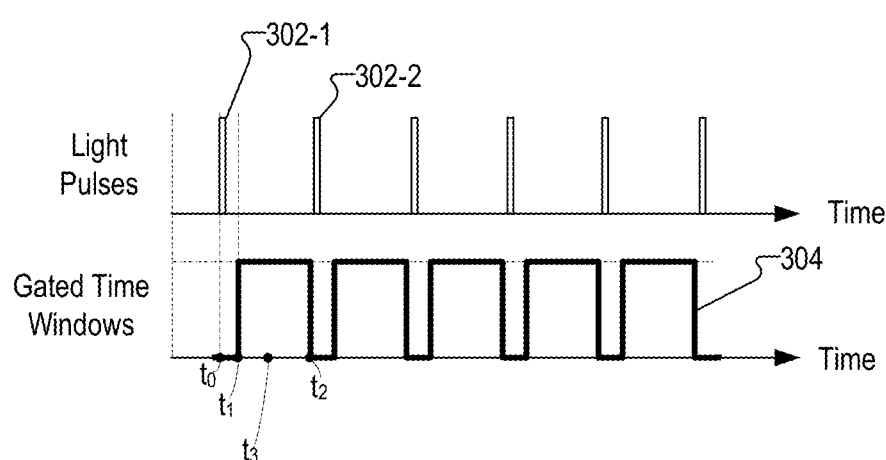
Fig. 3

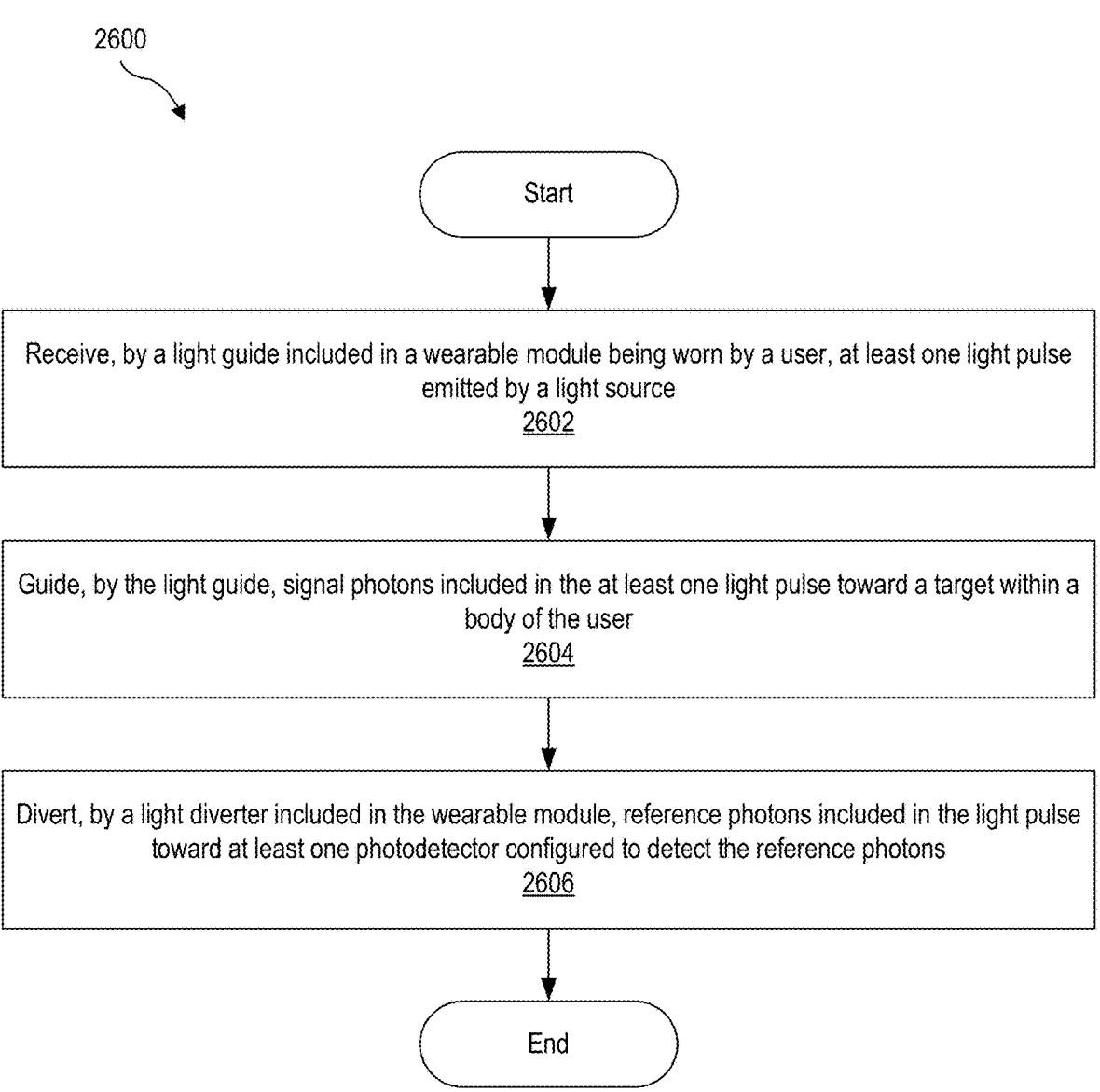

Start

Receive, by a light guide included in a wearable module being worn by a user, at least one light pulse emitted by a light source
2602

Guide, by the light guide, signal photons included in the at least one light pulse toward a target within a body of the user
2604

Divert, by a light diverter included in the wearable module, reference photons included in the light pulse toward at least one photodetector configured to detect the reference photons
2606

End

TIME DOMAIN-BASED OPTICAL MEASUREMENT SYSTEMS AND METHODS CONFIGURED TO MEASURE ABSOLUTE PROPERTIES OF TISSUE

RELATED APPLICATIONS

The present application is a continuation of U.S. patent application Ser. No. 17/176,560, filed Feb. 16, 2021, which claims priority under 35 U.S.C. § 119(e) to U.S. Provisional Patent Application No. 63/064,688, filed Aug. 12, 2020, and to U.S. Provisional Patent Application No. 63/012,538, filed Apr. 20, 2020, and to U.S. Provisional Patent Application No. 62/979,866, filed Feb. 21, 2020. These applications are incorporated herein by reference in their respective entireties.

BACKGROUND INFORMATION

Detecting neural activity in the brain (or any other turbid medium) is useful for medical diagnostics, imaging, neuro-engineering, brain-computer interfacing, and a variety of other diagnostic and consumer-related applications. For example, it may be desirable to detect neural activity in the brain of a user to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

Neural activity and other attributes of the brain may be determined or inferred by measuring responses of tissue within the brain to light pulses. One technique to measure such responses is time-correlated single-photon counting (TCSPC). Time-correlated single-photon counting detects single photons and measures a time of arrival of the photons with respect to a reference signal (e.g., a light source). By repeating the light pulses, TCSPC may accumulate a sufficient number of photon events to statistically determine a histogram representing the distribution of detected photons. Based on the histogram of photon distribution, the response of tissue to light pulses may be determined in order to study the detected neural activity and/or other attributes of the brain.

In the red/near-infrared spectrum (e.g., 650 nanometers (nm) to 900 nm), the two main physical phenomena that affect photon trajectory and, hence, photon arrival time are scattering and absorption; photons that are not absorbed are scattered, and a portion of the scattered photons may be detected. The main absorbing chromophores within tissue are hemoglobin, which can either be bound to oxygen (oxygenated hemoglobin, or $HbO2$), or not bound to oxygen (deoxygenated hemoglobin, or $HHb$). Time resolved near-infrared spectroscopy (TR-NIRS) may be used to quantify the absolute concentrations of these two chromophores ($[HbO2]$ and $[HHb]$), and changes in their concentrations, due to their well-distinguished optical spectra.

TR-NIRS may also be used to detect a third chromophore, cytochrome-c-oxidase (CCO), present in the tissue. CCO drives the electron transport chain in the mitochondria, which is responsible for approximately 95% of cellular oxygen metabolism. The ability to monitor changes in the oxidation state of CCO (e.g., oxidized CCO, or "oxCCO") in combination with hemoglobin measurements can give a full picture of oxidative metabolism, and thus tissue function. However, measuring the absolute concentration of oxCCO ([oxCCO]), and changes in the concentration of oxCCO, is challenging because the concentration of oxCCO is significantly lower than that of hemoglobin, and the contrast of oxCCO is dominated by a broad absorption peak around 820-850 nm.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 2 illustrates an exemplary detector architecture.

FIG. 3 illustrates an exemplary timing diagram for performing an optical measurement operation using an optical measurement system.

FIGS. 8 and 9 illustrate cross-sectional views of the wearable module of FIGS. 6A-7B, including an exemplary light source assembly included in the wearable module, taken along the dash-dot-dash line labeled XIII-XIII in FIG. 7A.

FIGS. 26 and 27 illustrate exemplary methods.

DETAILED DESCRIPTION

Figure 1:
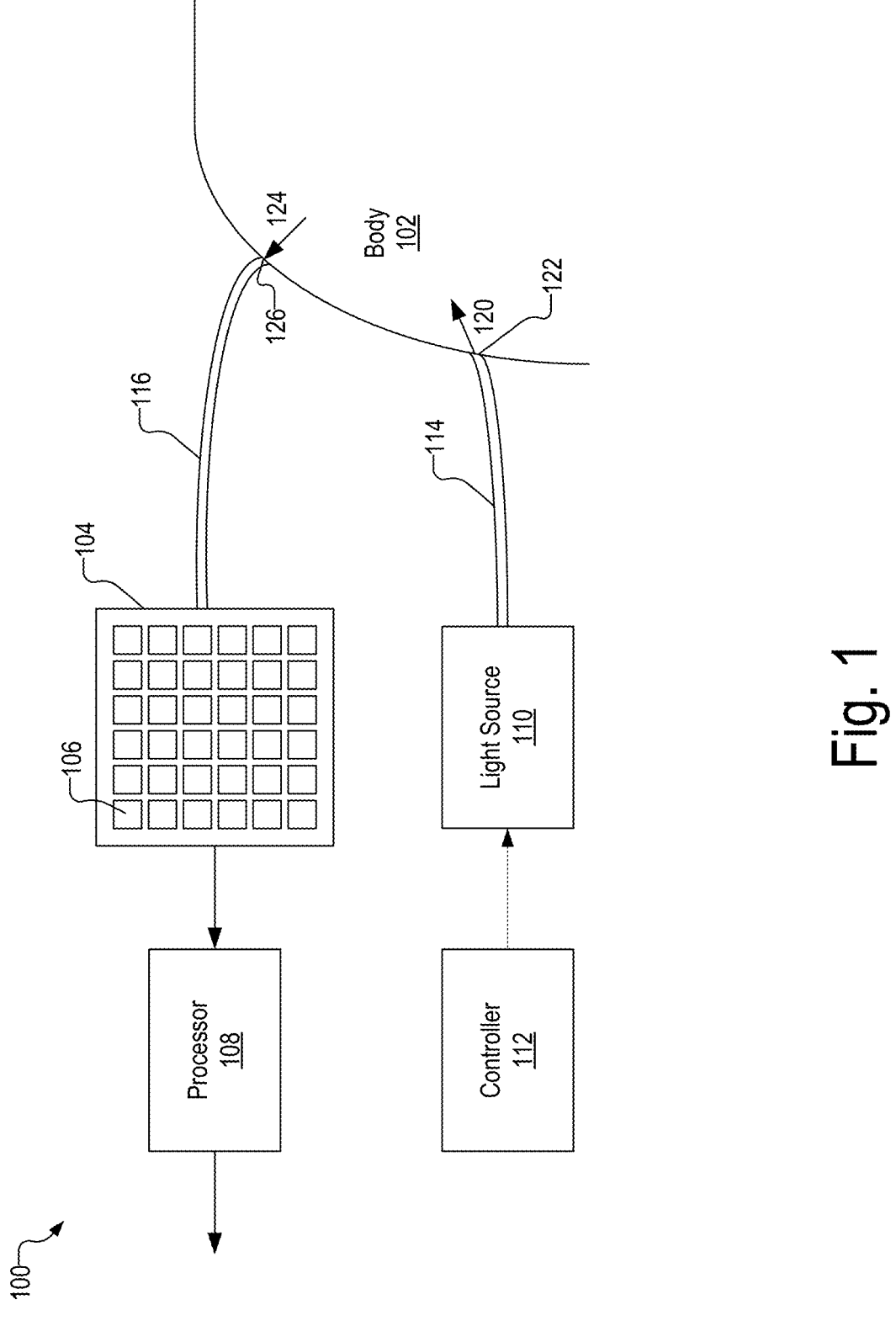
FIG. 1 illustrates an exemplary optical measurement system.

Wearable modules and optical measurement systems are described herein. For example, a wearable module for use in an optical measurement system may include a light guide and a light diverter. The light guide is configured to receive a light pulse from a light source and guide signal photons included in the light pulse toward a target within a body of a user. The light diverter is configured to divert reference photons included in the light pulse toward at least one photodetector configured to detect the signal photons and the reference photons. A processing unit of an optical measurement system may determine a temporal distribution of the signal photons detected by the at least one photodetector and determine a temporal distribution of the reference photons detected by the at least one photodetector. The processing unit may generate a histogram based on the temporal distribution of the signal photons and the temporal distribution of the reference photons.

The apparatuses, systems, and methods described herein provide various benefits and advantages compared with conventional optical measurement approaches. For example, in the histogram generated by the processing unit, the temporal distribution of the reference photons serves as a reference of the timing of the emitted light pulse that produces the temporal distribution of signal photons. Accordingly, the temporal distribution of signal photons can be calculated relative to the temporal distribution of reference photons. As a result, the temporal distribution of signal photons can be shifted in time to when the light source was actually fired (e.g., when the emitted light entered the target). This allows the histogram to be used to calculate various attributes, such as the absolute measure of the pathlength of the signal photons through the target (e.g., tissue) and the absolute measures of the reduced scattering coefficient $\mu_s'$ and absorption coefficient $\mu_a$ of the target.

With the absolute measures of the optical pathlength, scattering coefficient $\mu_s'$, and absorption coefficient $\mu_a$ of the target, absolute values of chromophore concentrations (e.g., [HbO2], [HHb], and [oxCCO]) and accurate scaling of changes in concentrations of these chromophores can be determined simultaneously in accordance with the principles described herein. Having absolute pathlength and accurate scaling of concentration changes of chromophores allows for an appropriate solve of the modified Beer-Lambert equation, which leads to less crosstalk with hemoglobin when measuring the absolute oxCCO concentration ([oxCCO]), more accuracy in the chromophore measurements, and a higher-fidelity optical measurement system over conventional NIRS systems.

Additionally, the apparatuses, systems, and methods described herein enable detection of cerebral changes in [HbO2], [HHb], and [oxCCO] simultaneously. The ability to monitor changes in the oxidation state of CCO (e.g., [oxCCO]) simultaneously with [HbO2] and [HHb] measurements) may provide a full picture of oxidative metabolism and tissue function. Moreover, the apparatuses, systems, and methods described herein can provide this information simultaneously with neural activity information (e.g., electroencephalography (EEG) recordings, magnetoencephalography (MEG) recordings, etc.). Additionally, the [HbO2], [HHb], [oxCCO], and neural activity information can be provided by a wearable, whole-head coverage format, thereby measuring brain health and activity across the entire brain. The systems and apparatuses described herein are also more compact and more comfortable to the user than conventional systems and apparatuses, thereby facilitating the acquisition of brain health and activity across a wide range of user activities.

The apparatuses, systems, and methods described herein can also help build models for neurovascular and neurometabolic coupling. Additionally, the apparatuses, systems, and methods described herein may provide a set of simultaneously captured features that can enhance statistical models for brain activity decoding and biomarker exploration for brain state and neurodegenerative disorders. For example, in Alzheimer's disease, regional hypometabolism in the brain is a predictor for progressive cognitive decline, and reduced cerebral metabolism is associated with carriers of the Alzheimer's disease risk. Having a full picture of oxidative metabolism and neural activity can also help identify brain trauma and the progression of recovery. In the realm of neurovascular coupling, a rich data set capturing [HbO2], [HHb], [oxCCO], and neural firing simultaneously and in vivo can generate a model that accurately describes the correlation between blood flow and neural firing, to which such a model can be highly advantageous to predicting changes in brain state and cognition.

These and other advantages and benefits of the present apparatuses, systems, and methods are described more fully herein and/or will be made apparent in the description herein.

FIG. 1 shows an exemplary optical measurement system 100 configured to perform an optical measurement operation with respect to a body 102. Optical measurement system 100 may, in some examples, be portable and/or wearable by a user.

In some examples, optical measurement operations performed by optical measurement system 100 are associated with a time domain-based optical measurement technique. Example time domain-based optical measurement techniques include, but are not limited to, TCSPC, time domain near infrared spectroscopy (TD-NIRS), time domain diffusive correlation spectroscopy (TD-DCS), and time domain digital optical tomography (TD-DOT).

As shown, optical measurement system 100 includes a detector 104 that includes a plurality of individual photodetectors (e.g., photodetector 106), a processor 108 coupled to detector 104, a light source 110, a controller 112, and optical conduits 114 and 116 (e.g., light guides, as described more fully herein). However, one or more of these components may not, in certain embodiments, be considered to be a part of optical measurement system 100. For example, in implementations where optical measurement system 100 is wearable by a user, processor 108 and/or controller 112 may in some embodiments be separate from optical measurement system 100 and not configured to be worn by the user.

Detector 104 may include any number of photodetectors 106 as may serve a particular implementation, such as $2^n$ photodetectors (e.g., 256, 512, . . . , 16384, etc.), where n is an integer greater than or equal to one (e.g., 4, 5, 8, 10, 11, 14, etc.). Photodetectors 106 may be arranged in any suitable manner.

Photodetectors 106 may each be implemented by any suitable circuit configured to detect individual photons of light incident upon photodetectors 106. For example, each photodetector 106 may be implemented by a single photon avalanche diode (SPAD) circuit and/or other circuitry as may serve a particular implementation.

Processor 108 may be implemented by one or more physical processing (e.g., computing) devices. In some examples, processor 108 may execute instructions (e.g., software) configured to perform one or more of the operations described herein.

Light source 110 may be implemented by any suitable component configured to generate and emit light. For example, light source 110 may be implemented by one or more laser diodes, distributed feedback (DFB) lasers, super luminescent diodes (SLDs), light emitting diodes (LEDs), diode-pumped solid-state (DPSS) lasers, super luminescent light emitting diodes (sLEDs), vertical-cavity surface-emitting lasers (VCSELs), titanium sapphire lasers, micro light emitting diode (mLEDs), and/or any other suitable laser or light source configured to emit light in one or more discrete wavelengths or narrow wavelength bands. In some examples, the light emitted by light source 110 is high coherence light (e.g., light that has a coherence length of at least 5 centimeters) at a predetermined center wavelength. In some examples, the light emitted by light source 110 is emitted as a plurality of alternating light pulses of different wavelengths.

Light source 110 is controlled by controller 112, which may be implemented by any suitable computing device (e.g., processor 108), integrated circuit, and/or combination of hardware and/or software as may serve a particular implementation. In some examples, controller 112 is configured to control light source 110 by turning light source 110 on and off and/or setting an intensity of light generated by light source 110. Controller 112 may be manually operated by a user, or may be programmed to control light source 110 automatically.

Light emitted by light source 110 travels via an optical conduit 114 (e.g., a light pipe, a light guide, a waveguide, a single-mode optical fiber, and/or or a multi-mode optical fiber) to body 102 of a subject. Body 102 may include any suitable turbid medium. For example, in some implementations, body 102 is a head or any other body part of a human or other animal. Alternatively, body 102 may be a non-living object. For illustrative purposes, it will be assumed in the examples provided herein that body 102 is a human head.

As indicated by arrow 120, light emitted by light source 110 enters body 102 at a first location 122 on body 102. Accordingly, a distal end of optical conduit 114 may be positioned at (e.g., right above, in physical contact with, or physically attached to) first location 122 (e.g., to a scalp of the subject). In some examples, the light may emerge from optical conduit 114 and spread out to a certain spot size on body 102 to fall under a predetermined safety limit. At least a portion of light indicated by arrow 120 may be scattered within body 102.

As used herein, "distal" means nearer, along the optical path of the light emitted by light source 110 or the light received by detector 104, to the target (e.g., within body 102) than to light source 110 or detector 104. Thus, the distal end of optical conduit 114 is nearer to body 102 than to light source 110, and the distal end of optical conduit 116 is nearer to body 102 than to detector 104. Additionally, as used herein, "proximal" means nearer, along the optical path of the light emitted by light source 110 or the light received by detector 104, to light source 110 or detector 104 than to body 102. Thus, the proximal end of optical conduit 114 is nearer to light source 110 than to body 102, and the proximal end of optical conduit 116 is nearer to detector 104 than to body 102.

As shown, the distal end of optical conduit 116 (e.g., a light pipe, a light guide, a waveguide, a single-mode optical fiber, and/or a multi-mode optical fiber) is positioned at (e.g., right above, in physical contact with, or physically attached to) output location 126 on body 102. In this manner, optical conduit 116 may collect at least a portion of the scattered light (indicated as light 124) as it exits body 102 at location 126 and carry light 124 to detector 104. Light 124 may pass through one or more lenses and/or other optical elements (not shown) that direct light 124 onto each of the photodetectors 106 included in detector 104.

Photodetectors 106 may be connected in parallel in detector 104. An output of each of photodetectors 106 may be accumulated to generate an accumulated output of detector 104. Processor 108 may receive the accumulated output and determine, based on the accumulated output, a temporal distribution of photons detected by photodetectors 106. Processor 108 may then generate, based on the temporal distribution, a histogram representing a light pulse response of a target (e.g., tissue, blood flow, etc.) in body 102. Example embodiments of accumulated outputs are described herein.

FIG. 2 illustrates an exemplary detector architecture 200 that may be used in accordance with the systems and methods described herein. As shown, architecture 200 includes a SPAD circuit 202 that implements photodetector 106, a control circuit 204, a time-to-digital converter (TDC) 206, and a signal processing circuit 208. Architecture 200 may include additional or alternative components as may serve a particular implementation.

In some examples, SPAD circuit 202 includes a SPAD and a fast gating circuit configured to operate together to detect a photon incident upon the SPAD. As described herein, SPAD circuit 202 may generate an output when SPAD circuit 202 detects a photon.

The fast gating circuit included in SPAD circuit 202 may be implemented in any suitable manner. For example, the fast gating circuit may include a capacitor that is pre-charged with a bias voltage before a command is provided to arm the SPAD. Gating the SPAD with a capacitor instead of with an active voltage source, such as is done in some conventional SPAD architectures, has a number of advantages and benefits. For example, a SPAD that is gated with a capacitor may be armed practically instantaneously compared to a SPAD that is gated with an active voltage source. This is because the capacitor is already charged with the bias voltage when a command is provided to arm the SPAD. This is described more fully in U.S. Pat. Nos. 10,158,038 and 10,424,683, which are incorporated herein by reference in their entireties.

In some alternative configurations, SPAD circuit 202 does not include a fast gating circuit. In these configurations, the SPAD included in SPAD circuit 202 may be gated in any suitable manner.

Control circuit 204 may be implemented by an application specific integrated circuit (ASIC) or any other suitable circuit configured to control an operation of various components within SPAD circuit 202. For example, control circuit 204 may output control logic that puts the SPAD included in SPAD circuit 202 in either an armed or a disarmed state.

In some examples, control circuit 204 may control a gate delay, which specifies a predetermined amount of time control circuit 204 is to wait after an occurrence of a light pulse (e.g., a laser pulse) to put the SPAD in the armed state. To this end, control circuit 204 may receive light pulse timing information, which indicates a time at which a light pulse occurs (e.g., a time at which the light pulse is applied to body 102). Control circuit 204 may also control a programmable gate width, which specifies how long the SPAD is kept in the armed state before being disarmed.

Control circuit 204 is further configured to control signal processing circuit 208. For example, control circuit 204 may provide histogram parameters (e.g., time bins, number of light pulses, type of histogram, etc.) to signal processing circuit 208. Signal processing circuit 208 may generate histogram data in accordance with the histogram parameters. In some examples, control circuit 204 is at least partially implemented by controller 112.

TDC 206 is configured to measure a time difference between an occurrence of an output pulse generated by SPAD circuit 202 and an occurrence of a light pulse. To this end, TDC 206 may also receive the same light pulse timing information that control circuit 204 receives. TDC 206 may be implemented by any suitable circuitry as may serve a particular implementation.

Signal processing circuit 208 is configured to perform one or more signal processing operations on data output by TDC 206. For example, signal processing circuit 208 may generate histogram data based on the data output by TDC 206 and in accordance with histogram parameters provided by control circuit 204. To illustrate, signal processing circuit 208 may generate, store, transmit, compress, analyze, decode, and/or otherwise process histograms based on the data output by TDC 206. In some examples, signal processing circuit 208 may provide processed data to control circuit 204, which may use the processed data in any suitable manner. In some examples, signal processing circuit 208 is at least partially implemented by processor 108.

In some examples, each photodetector 106 (e.g., SPAD circuit 202) may have a dedicated TDC 206 associated therewith. For example, for an array of N photodetectors 106, there may be a corresponding array of N TDCs 206. Alternatively, a single TDC 206 may be associated with multiple photodetectors 106. Likewise, a single control circuit 204 and a single signal processing circuit 208 may be provided for one or more SPAD circuits 202 and/or TDCs 206.

FIG. 3 illustrates an exemplary timing diagram 300 for performing an optical measurement operation using optical measurement system 100. The optical measurement operation may be performed in accordance with a time domain-based technique, such as TD-NIRS. Optical measurement system 100 may be configured to perform the optical measurement operation by directing light pulses (e.g., laser pulses) toward a target within a body (e.g., body 102). The light pulses may be short (e.g., 10-2000 picoseconds (ps)) and repeated at a high frequency (e.g., between 100,000 hertz (Hz) and 100 megahertz (MHz)). The light pulses may be scattered by the target and at least a portion of the scattered light may be detected by optical measurement system 100. Optical measurement system 100 may measure a time relative to the light pulse for each detected photon. By counting the number of photons detected at each time relative to each light pulse repeated over a plurality of light pulses, optical measurement system 100 may generate a histogram that represents a light pulse response of the target (e.g., a temporal point spread function (TPSF)). The terms histogram and TPSF are used interchangeably herein to refer to a light pulse response of a target.

Timing diagram 300 shows a sequence of light pulses 302 (e.g., light pulses 302-1 and 302-2) that may be applied to the target (e.g., tissue within a brain of a user, blood flow, a fluorescent material used as a probe in a body of a user, etc.). Timing diagram 300 also shows a pulse wave 304 representing predetermined gated time windows (also referred as gated time periods) during which photodetectors 106 are gated ON to detect photons. As shown, light pulse 302-1 is applied at a time $t_0$. At a time $t_1$, a first instance of the predetermined gated time window begins. Photodetectors 106 may be armed at time $t_1$, enabling photodetectors 106 to detect photons scattered by the target during the predetermined gated time window. In this example, time $t_1$ is set to be at a certain time after time $t_0$, which may minimize photons detected directly from the laser pulse, before the laser pulse reaches the target. However, in some alternative examples, time $t_1$ is set to be equal to time $t_0$.

At a time $t_2$, the predetermined gated time window ends. In some examples, photodetectors 106 may be disarmed at time $t_2$. In other examples, photodetectors 106 may be reset (e.g., disarmed and re-armed) at time $t_2$ or at a time subsequent to time $t_2$. During the predetermined gated time window, photodetectors 106 may detect photons scattered by the target. Photodetectors 106 may be configured to remain armed during the predetermined gated time window such that photodetectors 106 maintain an output upon detecting a photon during the predetermined gated time window. For example, a photodetector 106 may detect a photon at a time $t_3$, which is during the predetermined gated time window between times $t_1$ and $t_2$. The photodetector 106 may be configured to provide an output indicating that the photodetector 106 has detected a photon. The photodetector 106 may be configured to continue providing the output until time $t_2$, when the photodetector may be disarmed and/or reset. Optical measurement system 100 may generate an accumulated output from the plurality of photodetectors. Optical measurement system 100 may sample the accumulated output to determine times at which photons are detected by photodetectors 106 to generate a TPSF.

Figure 4:
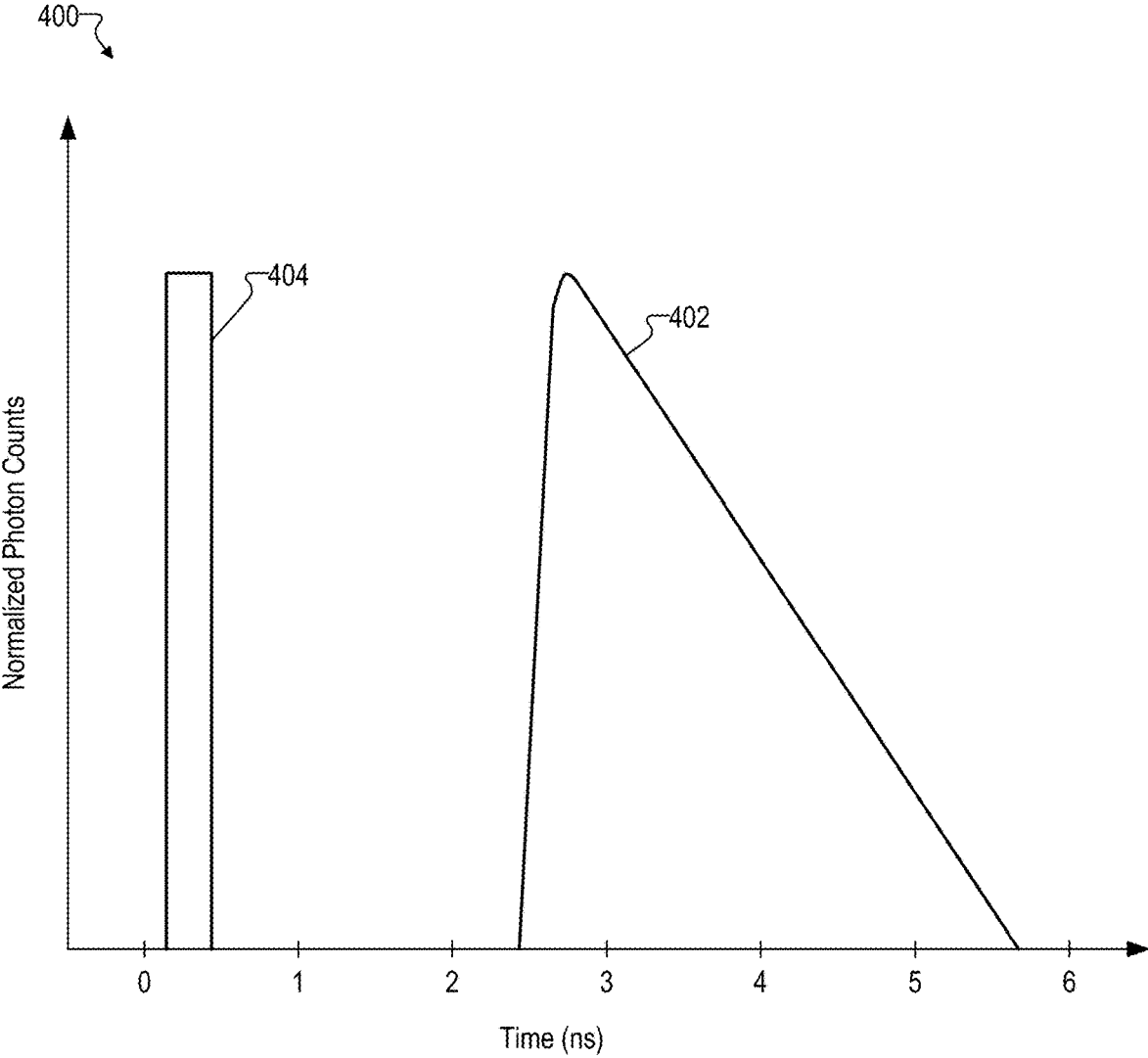
FIG. 4 illustrates a graph of an exemplary temporal point spread function that may be generated by an optical measurement system in response to a light pulse.

FIG. 4 illustrates a graph 400 of an exemplary TPSF 402 that may be generated by optical measurement system 100 in response to a light pulse 404 (which, in practice, represents a plurality of light pulses). Graph 400 shows a normalized count of photons on a y-axis and time bins on an x-axis. As shown, TPSF 402 is delayed with respect to a temporal occurrence of light pulse 404. In some examples, the number of photons detected in each time bin subsequent to each occurrence of light pulse 404 may be aggregated (e.g., integrated) to generate TPSF 402. TPSF 402 may be analyzed and/or processed in any suitable manner to determine or infer biological (e.g., neural) activity.

Optical measurement system 100 may be implemented by or included in any suitable device(s). For example, optical measurement system 100 may be included in a non-wearable device (e.g., a medical device and/or consumer device that is placed near the head or other body part of a user to perform one or more diagnostic, imaging, and/or consumer-related operations). Optical measurement system 100 may alternatively be included, in whole or in part, in a sub-assembly enclosure of a wearable invasive device (e.g., an implantable medical device for brain recording and imaging).

Alternatively, optical measurement system 100 may be included, in whole or in part, in a non-invasive wearable device that a user may wear to perform one or more diagnostic, imaging, analytical, and/or consumer-related operations. The non-invasive wearable device may be placed on a user's head or other part of the user to detect neural activity. In some examples, such neural activity may be used to make behavioral and mental state analysis, awareness and predictions for the user.

Mental state described herein refers to the measured neural activity related to physiological brain states and/or mental brain states, e.g., joy, excitement, relaxation, surprise, fear, stress, anxiety, sadness, anger, disgust, contempt, contentment, calmness, focus, attention, approval, creativity, positive or negative reflections/attitude on experiences or the use of objects, etc. Further details on the methods and systems related to a predicted brain state, behavior, preferences, or attitude of the user, and the creation, training, and use of neuromes can be found in U.S. Provisional Patent Application No. 63/047,991, filed Jul. 3, 2020. Exemplary measurement systems and methods using biofeedback for awareness and modulation of mental state are described in more detail in U.S. patent application Ser. No. 16/364,338, filed Mar. 26, 2019, published as US2020/0196932A1. Exemplary measurement systems and methods used for detecting and modulating the mental state of a user using entertainment selections, e.g., music, film/video, are described in more detail in U.S. patent application Ser. No. 16/835,972, filed Mar. 31, 2020, published as US2020/0315510A1. Exemplary measurement systems and methods used for detecting and modulating the mental state of a user using product formulation from, e.g., beverages, food, selective food/drink ingredients, fragrances, and assessment based on product-elicited brain state measurements are described in more detail in U.S. patent application Ser. No. 16/853,614, filed Apr. 20, 2020, published as US2020/0337624A1. Exemplary measurement systems and methods used for detecting and modulating the mental state of a user through awareness of priming effects are described in more detail in U.S. patent application Ser. No. 16/885,596, filed May 28, 2020, published as US2020/0390358A1. These applications and corresponding U.S. publications are incorporated herein by reference in their entirety.

Figure 5:
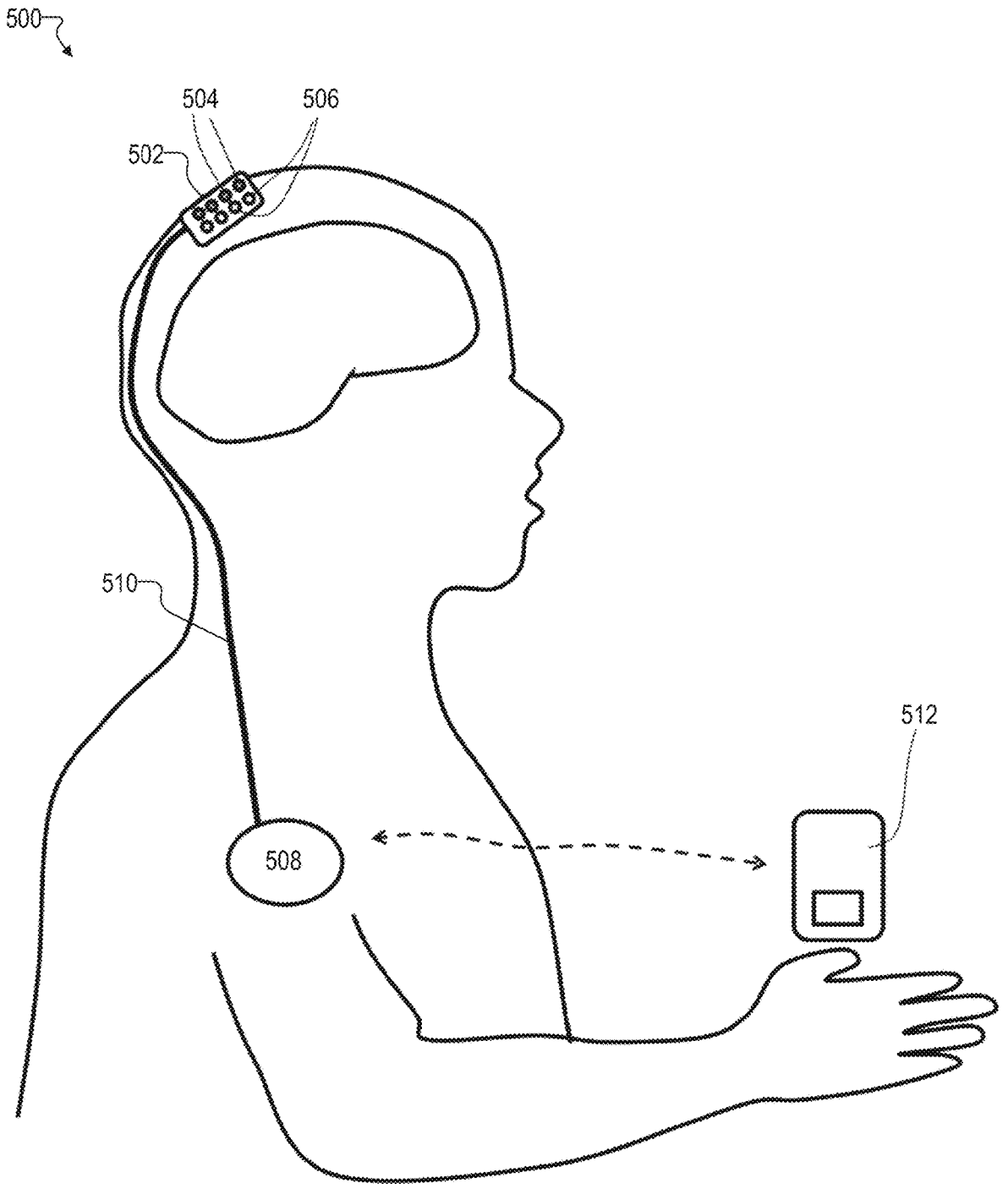
FIG. 5 illustrates an exemplary non-invasive wearable brain interface system.

FIG. 5 shows an exemplary non-invasive wearable brain interface system 500 ("brain interface system 500") that implements optical measurement system 100 (shown in FIG. 1). As shown, brain interface system 500 includes a head-mountable component 502 configured to be attached to and/or worn on a user's head. Head-mountable component 502 may be implemented by a cap shape that is worn on a head of a user. Alternative implementations of head-mountable component 502 include helmets, beanies, headbands, other hat shapes, or other forms conformable to be worn on a user's head, etc. Head-mountable component 502 may be made out of any suitable cloth, soft polymer, plastic, hard shell, and/or any other suitable material as may serve a particular implementation. Examples of headgears used with wearable brain interface systems are described below in more detail and in U.S. Pat. No. 10,340,408, incorporated herein by reference in its entirety.

Head-mountable component 502 includes a plurality of detectors 504, which may implement or be similar to detector 104, and a plurality of light sources 506, which may be implemented by or be similar to light source 110. It will be recognized that in some alternative embodiments, head-mountable component 502 may include a single detector 504 and/or a single light source 506.

Brain interface system 500 may be used for controlling an optical path to the brain and/or for transforming photodetector measurements into an intensity value that represents an optical property of a target within the brain. Brain interface system 500 allows optical detection of deep anatomical locations beyond skin and bone (e.g., skull) by extracting data from photons originating from light sources 506 and emitted to a target location within the user's brain, in contrast to conventional imaging systems and methods (e.g., optical coherence tomography (OCT), continuous wave near infrared spectroscopy (CW-NIRS)), which only image superficial tissue structures or through optically transparent structures.

Brain interface system 500 may further include a processor 508 configured to communicate with (e.g., control and/or receive signals from) detectors 504 and light sources 506 by way of a communication link 510. Communication link 510 may include any suitable wired and/or wireless communication link. Processor 508 may include any suitable housing and may be located on the user's scalp, neck, shoulders, chest, or arm, as may be desirable. In some variations, processor 508 may be integrated in the same assembly housing as detectors 504 and light sources 506. In some examples, processor 508 is implemented by or similar to processor 108 and/or controller 112.

As shown, brain interface system 500 may optionally include a remote processor 512 in communication with processor 508. For example, remote processor 512 may store measured data from detectors 504 and/or processor 508 from previous detection sessions and/or from multiple brain interface systems (not shown). In some examples, remote processor 512 is implemented by or similar to processor 108 and/or controller 112.

Power for detectors 504, light sources 506, and/or processor 508 may be provided via a wearable battery (not shown). In some examples, processor 508 and the battery may be enclosed in a single housing, and wires carrying power signals from processor 508 and the battery may extend to detectors 504 and light sources 506. Alternatively, power may be provided wirelessly (e.g., by induction).

In some alternative embodiments, head mountable component 502 does not include individual light sources. Instead, a light source configured to generate the light that is detected by detector 504 may be included elsewhere in brain interface system 500. For example, a light source may be included in processor 508 and/or in another wearable or non-wearable device and coupled to head mountable component 502 through an optical connection.

In some alternative embodiments, head mountable component 502 does not include individual detectors 504. Instead, one or more detectors configured to detect the scattered light from the target may be included elsewhere in brain interface system 500. For example, a detector may be included in processor 508 and/or in another wearable or non-wearable device and coupled to head mountable component 502 through an optical connection.

Optical measurement system 100 may be modular in that one or more components of optical measurement system 100 may be removed, changed out, or otherwise modified as may serve a particular implementation. Additionally or alternatively, optical measurement system 100 may be modular such that one or more components of optical measurement system 100 may be housed in a separate housing (e.g., module) and/or may be movable relative to other components. Exemplary modular optical measurement systems are described in more detail in U.S. Provisional Patent Application No. 63/081,754, filed Sep. 22, 2020, U.S. Provisional Patent Application No. 63/038,459, filed Jun. 12, 2020, U.S. Provisional Patent Application No. 63/038,468, filed Jun. 12, 2020, U.S. Provisional Patent Application No. 63/038, 481, filed Jun. 12, 2020, and U.S. Provisional Patent Application No. 63/064,688, filed Aug. 12, 2020, which applications are incorporated herein by reference in their respective entireties.

Figure 6A:
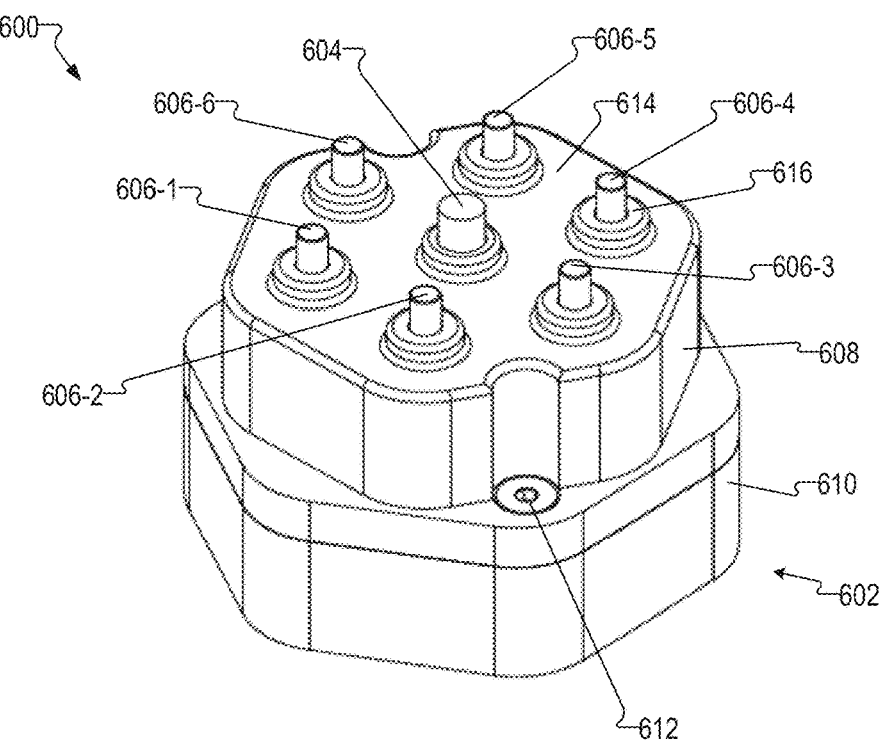
FIGS. 6A, 6B, 7A, and 7B illustrate various views of an exemplary wearable module that may be used in an optical measurement system.
Figure 6B:
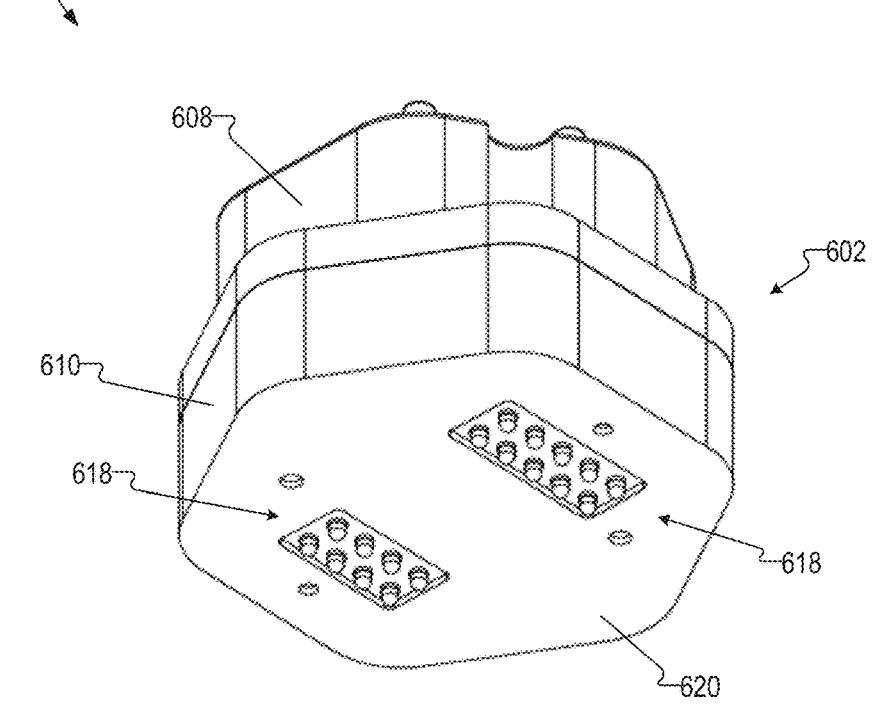
Figure 7A:
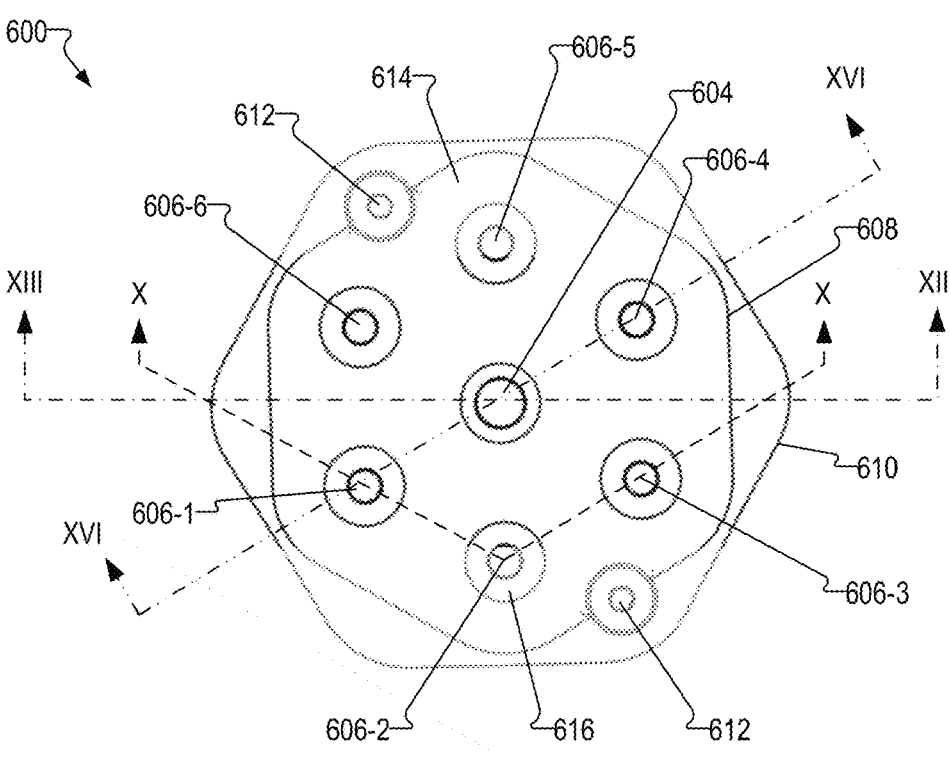
Figure 7B:
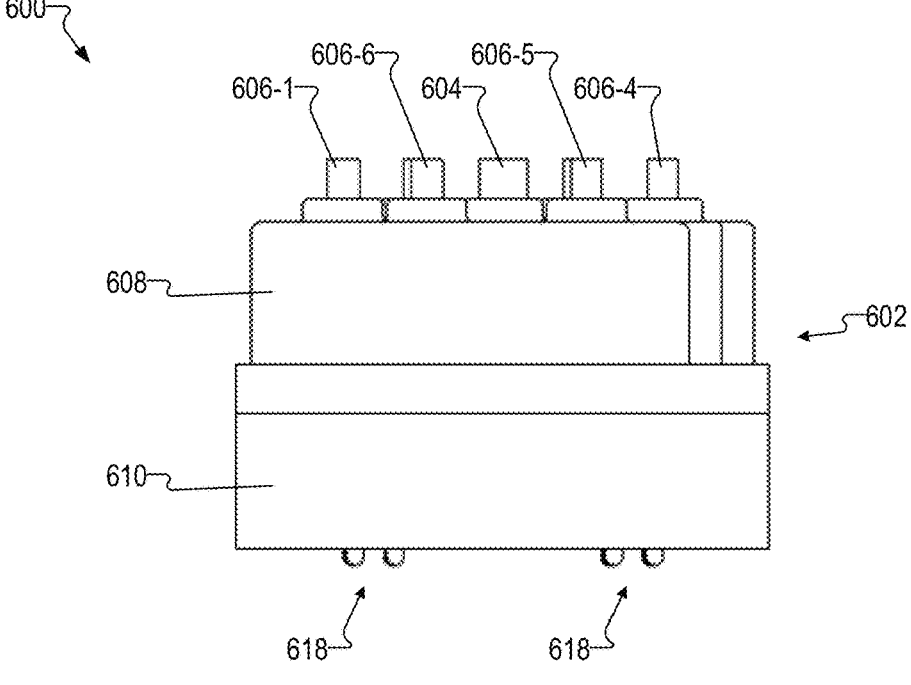

As mentioned, one or more components of optical measurement system 100 (e.g., head-mountable component 502) may be implemented in a wearable module. FIGS. 6A-7B illustrate various views of an exemplary wearable module 600 ("module 600") that may implement one or more components of optical measurement system 100. FIG. 6A shows a perspective view of a top side of module 600, FIG. 6B shows a perspective view of a bottom side of module 600, FIG. 7A shows a plan view of the top side of module 600, and FIG. 7B shows a side view of module 600. In some examples, module 600 may be included in a head-mountable component (e.g., head-mountable component 502) of an optical measurement system (e.g., brain interface system 500).

As shown in FIGS. 6A-7B, module 600 includes a housing 602, a light-emitting member 604, and a plurality of light-receiving members 606 (e.g., light-receiving members 606-1 through 606-6). Module 600 may include any additional or alternative components as may suit a particular implementation.

Housing 602 is configured to support and/or house various components of module 600, including light-emitting member 604 and light-receiving members 606 as well any other components of module 600 not shown in FIGS. 6A-7B (e.g., various components of a light source assembly and/or a plurality of detector assemblies, a controller, a processor, a signal processing circuit, etc.). As shown, housing 602 includes an upper housing 608 and a lower housing 610 joined and held together by fasteners 612 (e.g., screws, bolts, etc.). As used herein with reference to module 600, "upper" refers to a side of module 600 that faces a target within a body of a user when module 600 is worn by the user, and "lower" refers to a side of module 600 that is farthest from the target when module 600 is worn by the user. Light-emitting member 604 and light-receiving members 606 protrude from an upper surface 614 (a target-side surface) of upper housing 608 so that light may be emitted toward and received from the target.

In some examples, as shown in FIGS. 6A, 7A, and 7B, upper housing 608 includes a plurality of frame supports 616 protruding from upper surface 614 and configured to support light-emitting member 604 and light-receiving members 606 in a lateral direction. Frame supports 616 may be formed integrally with upper surface 614 or may be formed separately and attached to upper surface 614.

As shown in FIGS. 6A-7B, upper housing 608 and lower housing 610 have a generally hexagonal shape, and are rotationally offset from one another (e.g., by about 30°). It will be recognized that upper housing 608 and lower housing 610 may alternatively be aligned with one another (rather than rotationally offset), and may alternatively have any other shape as may suit a particular implementation (e.g., rectangular, square, circular, triangular, pentagonal, free-form, etc.). However, a hexagonal shape, along with beveled and/or rounded edges and corners, allows a plurality of modules to be flexibly interconnected adjacent one another in a wearable module assembly (e.g., in a head-mountable component). Thus, a wearable module assembly may conform to three-dimensional surface geometries, such as a user's head. Exemplary wearable module assemblies comprising a plurality of wearable modules are described in more detail in U.S. Provisional Patent Application No. 62/992,550, filed Mar. 20, 2020, U.S. Provisional Patent Application No. 63/038,459, filed Jun. 12, 2020, and U.S. Provisional Patent Application No. 63/038,468, filed Jun. 12, 2020, which applications are incorporated herein by reference in their respective entireties.

Light-emitting member 604 (e.g., a light-emitting light guide) is configured to emit light (e.g., light 120, light pulses 302, or light pulse 404) from a distal end (e.g., an upper surface) of light-emitting member 604. Light-emitting member 604 may be implemented by any suitable optical conduit (e.g., optical conduit 114). Light-emitting member 604 is included in a light source assembly that is configured to generate and emit the light toward the target. In the examples shown in FIGS. 6A-7B, the light source assembly is included entirely within module 600. In alternative examples, one or more components of the light source assembly (e.g., light source 110, controller 112, etc.) are located off module 600 and connected (e.g., optically and/or electrically) with components in module 600 (e.g., with light-emitting member 604, etc.). Exemplary light source assemblies that may be included in module 600 will be described below in more detail.

When module 600 is worn by a user, a portion of the light emitted by light-emitting member 604 may be scattered by a target within the body of the user, and a portion of the scattered light (e.g., light 124) may be received by one or more light-receiving members 606 (e.g., one or more light-emitting light guides). Light-receiving members 606 may be implemented by any suitable optical conduit (e.g., optical conduit 116) and/or any other suitable means for conveying light. Light-receiving members 606 are included in a detector assembly configured to receive the scattered light and convey the scattered light (e.g., photons) to a photodetector (e.g., photodetector 106). In the examples shown in FIGS. 6A-7B, the detector assembly is included entirely within module 600. In alternative examples, one or more components of the detector assembly (e.g., detector 104, photodetector 106, processor 108, control circuit 204, TDC 206, signal processing circuit 208, etc.) are located off module 600 and connected (e.g., optically and/or electrically) with components in module 600 (e.g., with light-receiving members 606). Exemplary detector assemblies that may be included in module 600 will be described below in more detail.

As shown in FIG. 6B, module 600 further includes communication interfaces 618 on a lower surface 620 of lower housing 610. Communication interfaces 618 are configured to optically, electrically, and/or communicatively connect module 600 (e.g., components housed within housing 602) with other wearable modules, optical measurement system components (e.g., processor 508, remote processor 512, etc.), and/or any other remote components or devices (e.g., a remote computing device). In some examples, electrical power may be provided to module 600 by way of communication interface 618. Although communication interfaces 618 are shown to be positioned on lower surface 620, communication interfaces 618 may additionally or alternatively be positioned on any other surface of housing 602 as may suit a particular implementation. Additionally or alternatively, module 600 may include any suitable wireless communication interfaces.

Figure 8:
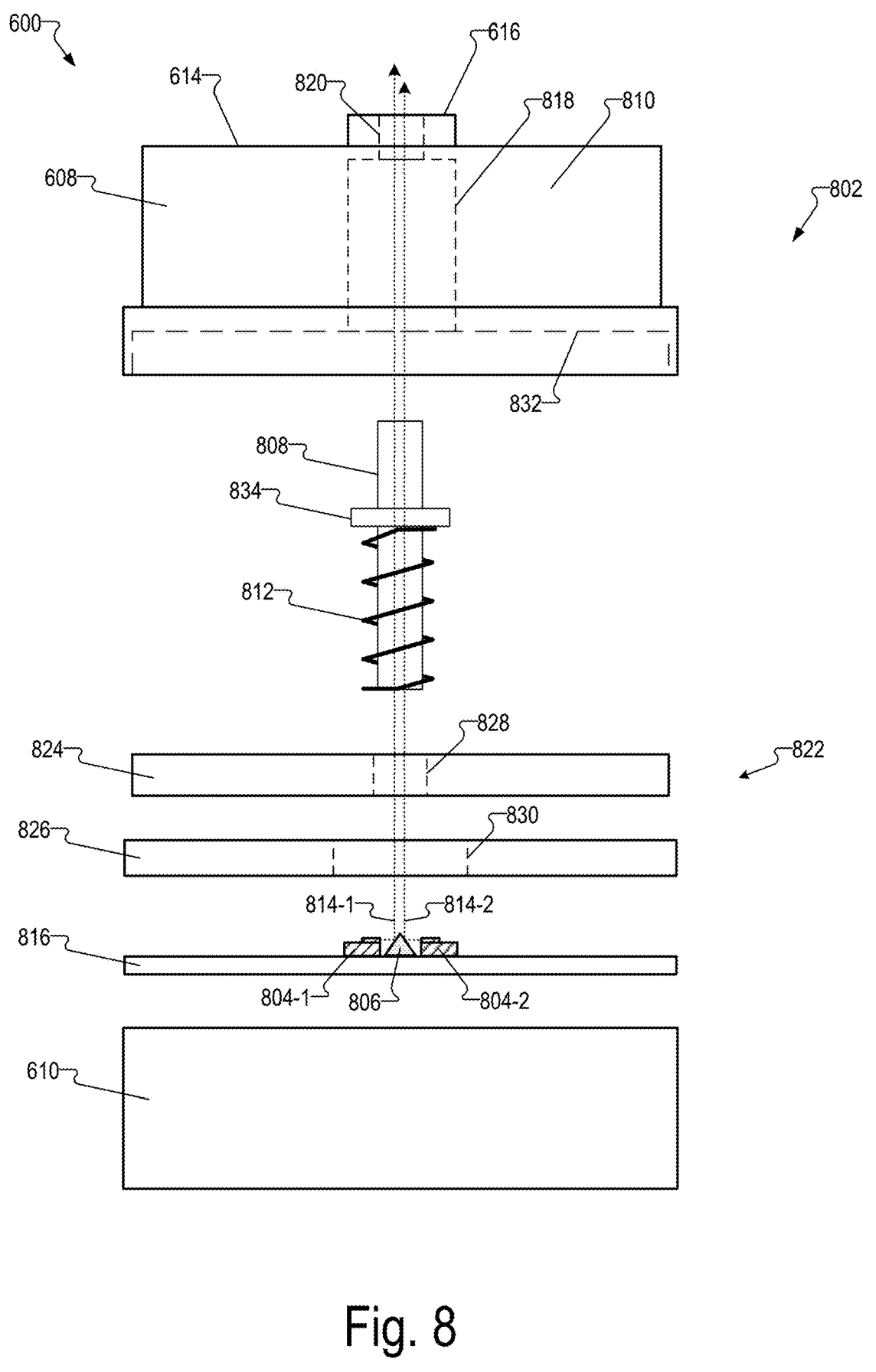
Figure 9:
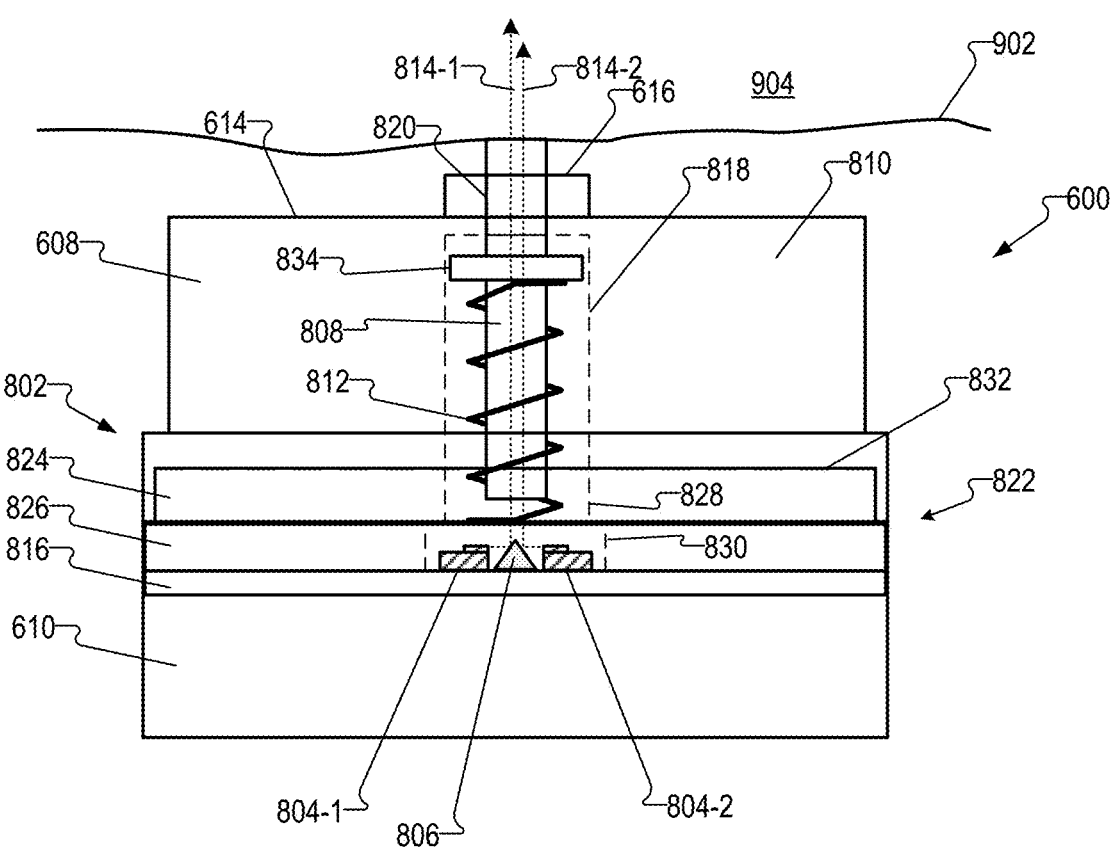

FIGS. 8 and 9 illustrate a cross-sectional view of module 600, including an exemplary light source assembly included in module 600, taken along the dash-dot-dash line labeled XIII-XIII shown in FIG. 7A. FIG. 8 shows an exploded view of module 600, and FIG. 9 shows a view of module 600 in an assembled state as worn by a user. As shown in FIGS. 8 and 9, module 600 includes a light source assembly 802 housed within housing 602. Module 600 may also include any other suitable components that are not shown in FIGS. 8 and 9, such as one or more detector assemblies described below in more detail.

In time domain-based optical measurement systems, such as systems based on TD-NIRS, alternating short light pulses of near-infrared (NIR) light in two or more wavelengths are emitted toward a target. A portion of the emitted light is scattered by the target while a portion of the light is absorbed by chromophores, such as by HbO2, HHb, and CCO.

Differences in the absorption spectra of HbO2, HHb, and CCO at different wavelengths can be measured and used to determine or infer biological activity (e.g., neural activity and/or cellular metabolism).

In conventional configurations of optical measurement systems, a light source capable of emitting light in a plurality of different wavelengths is located away from the user so that the emitted light must be conveyed from the light source to the wearable module by a relatively long optical fiber. This creates various problems. For example, the long optical fibers apply torque and other forces to the wearable module, often causing the wearable module to move and shift around when worn by the user. The movement of the wearable module can degrade the detected signal and the overall performance of the optical measurement system. Additionally, the heavy weight of the fibers can make the wearable module uncomfortable to wear. Furthermore, optical measurement systems using long fibers are large, expensive, and difficult to maintain.

To address these issues, light source assembly 802 included in module 600 includes a plurality of light sources 804 (e.g., a first light source 804-1 and a second light source 804-2), an optical member 806, and a light guide 808. Light source assembly 802 also includes a light guide block 810 and a spring member 812, but light guide block 810 and spring member 812 may be omitted in other embodiments. Moreover, while FIGS. 8 and 9 show two light sources 804 and one optical member 806, light source assembly 802 may include any other suitable number of light sources and/or optical members as may serve a particular implementation.

Each light source 804 is configured to emit light in a distinct wavelength. For example, first light source 804-1 is configured to emit first light 814-1 (e.g., one or more first light pulses) in a first wavelength and second light source 804-2 is configured to emit second light 814-2 (e.g., one or more second light pulses) in a second wavelength that is different from the first wavelength. The first wavelength and the second wavelength may each be a discrete wavelength or narrow wavelength band. For example, the first wavelength may be 750 nm and the second wavelength may be 850 nm. First light source 804-1 and second light source 804-2 may each be implemented by any suitable light source described herein, such as a laser diode configured to emit the first wavelength and the second wavelength, respectively. In some examples, light sources 804 may implement and/or be implemented by light source 110 and/or light source 506. Light sources 804 are disposed (e.g., mounted, attached, etc.) on a light source plate 816, such as but not limited to a printed circuit board ("PCB"). Light source plate 816 may be securely and immovably mounted within housing 602, such as by one or more fasteners (e.g., screws, bolts, snap-fit, etc.).

In the example shown in FIGS. 8 and 9, light sources 804 are configured to emit light 814 in a direction substantially parallel to a top surface of light sources 804 and/or light source plate 816. Accordingly, optical member 806 is disposed on light source plate 816 between light sources 804, and light sources 804 each emit light toward optical member 806. Optical member 806 may be any one or more devices configured to redirect light emitted from light sources 804 toward light guide 808. As shown in FIGS. 8 and 9, optical member 806 is a triangular reflecting prism configured to reflect light 814 at an angle of about 90°.

In alternative embodiments, optical member 806 may be a prism having any other shape (e.g., a 3- or 4-sided pyramid), a mirror, an optical conduit, a diffractive element, a lens, and/or any other suitable optical device that bends or redirects light. In some examples, light source assembly 802 includes a plurality of optical members each configured to redirect light emitted by a particular light source to light guide 808. Additionally or alternatively, light sources 804 may be configured to emit light in any other direction, such as a direction normal to an upper surface of light sources 804 and/or normal to light source plate 816. Accordingly, optical member 806 may be at any other location to receive the emitted light, such as above light sources 804.

Light guide 808 is configured to receive light 814 from optical member 806 and emit light 814 toward a target within a body of a user when module 600 is worn by a user. Light guide 808 may be implemented by any suitable optical conduit described herein. In some examples, light guide 808 implements or is implemented by optical conduit 114. As shown in FIGS. 8 and 9, light guide 808 comprises a rigid, elongate waveguide. In alternative examples, light guide 808 may comprise a bundle of optical fibers. A proximal end portion of light guide 808 is positioned nearest light sources 804 and optical member 806 and receives light 814 from optical member 806. A distal end portion of light guide 808 is configured to protrude from upper surface 614 of upper housing 608 and emit light 814 toward the target. With this configuration, a plurality of light pulses having a plurality of different wavelengths can be emitted toward the target from the same location.

Light guide 808 may be supported within module 600 in any suitable way. In some examples, as shown in FIGS. 8 and 9, light guide 808 is supported by light guide block 810 and spring member 812. Light guide block 810 may be a thick, solid member having a chamber 818 in which light guide 808 and spring member 812 are positioned. A proximal end of chamber 818 opens to the exterior of module 600 through an opening 820 in upper surface 614 and frame support 616. Light guide 808 is positioned within chamber 818 such that the distal end portion of light guide 808 is configured to protrude from upper surface 614 through opening 820. The distal end portion of light guide 808 protruding through opening 820 forms light-emitting member 604. In some examples, as shown in FIGS. 8 and 9, light guide block 810 is implemented by upper housing 608. In alternative embodiments, light guide block 810 is formed separately from upper housing 608 and is mounted inside upper housing 608.

As shown in FIGS. 8 and 9, a support assembly 822 may be positioned over a distal end portion of light guide block 810 to hold light guide 808 and spring member 812 within chamber 818. Support assembly 822 includes a first plate 824 (e.g., a lens plate of a detector assembly, described below in more detail) and a second plate 826 (e.g., a detector plate of the detector assembly). In some examples, support assembly 822 may also include light source plate 816. First plate 824 and second plate 826 include an opening 828 and an opening 830, respectively, to permit the passage of light 814 and/or accommodate light sources 804 and optical member 806. In some examples, light guide block 810 includes a recess portion 832 in which first plate 824 and/or second plate 826 may be positioned. While support assembly 822 is shown as being separate from first plate 824 and second plate 826, in alternative examples light source plate 816 may be implemented by first plate 824 and/or second plate 826. In additional or alternative examples, support assembly 822 includes only one plate.

In some examples, light guide 808 is configured to move within chamber 818 along an optical axis of light guide 808 (e.g., a longitudinal direction of chamber 818, which is a direction extending from the proximal end of chamber 818 to the distal end of chamber 818). Thus, the extent to which the distal end portion of light guide 808 protrudes from upper surface 614 can be adjusted in order to maintain light guide 808 in physical contact with the user's body.

Spring member 812 is configured to bias the distal end portion of light guide 808 away from upper surface 614. Thus, when module 600 is worn by a user, spring member 812 biases the distal end portion of light guide 808 toward a surface of a body (e.g., skin) of the user, thereby helping to ensure that the distal end portion of light guide 808 is in physical contact with the surface of the body. Spring member 812 may bias the distal end portion of light guide 808 away from upper surface 614 in any suitable way.

In some examples, as shown in FIGS. 8 and 9, spring member 812 comprises a coil spring positioned around an external surface light guide 808. A proximal end of spring member 812 pushes against first plate 824, while the distal end of spring member 812 pushes against a flange portion 834 protruding from a portion of light guide 808. Flange portion 834 may be any suitable structure (e.g., a ring) attached to or protruding from light guide 808. By pressing against flange portion 834, spring member 812 pushes the distal end of light guide 808 away from upper surface 614. In alternative embodiments, spring member 812 may be disposed on an upper side of flange portion 834 and configured to pull flange portion 834 (and hence light guide 808) toward the distal end of chamber 818. While FIGS. 8 and 9 show a coil spring, spring member 812 may be implemented by any other suitable device or mechanism configured to bias the distal end of light guide 808 away from upper surface 614 and toward the user's body.

Flange portion 834 has a width (e.g., diameter) approximately equal to a width (e.g., diameter) of chamber 818 (with sufficient tolerance to enable movement of light guide 808) to maintain a lateral position of light guide 808 within chamber 818. Similarly, opening 820 in upper surface 614 and frame support 616 has a width (e.g., diameter) approximately equal to a width (e.g., diameter) of light guide 808 (with sufficient tolerance to enable movement of light guide 808) to maintain a lateral position of light guide 808 within opening 820. With this configuration, a proximal end of light guide 808 may be maintained in optical alignment with optical member 806. In alternative examples, light source assembly 802 does not include spring member 812 or flange portion 834. For instance, chamber 818 may be approximately the same width (e.g., diameter) as light guide 808 and light guide 808 may be immovably attached to light guide block 810 within chamber 818.

To further maintain light guide 808 in optical alignment with optical member 806, as explained above, light source plate 816 is securely mounted within housing 602, thereby preventing movement of light sources 804 and optical member 806 relative to light guide 808.

In some examples, light source assembly 802 may include a controller (e.g., controller 112, processor 508, etc.) configured to control light sources 804 to output one or more light pulses. The controller may be located in any suitable location. In some examples, the controller may be disposed on light source plate 816, support assembly 822, or any other suitable location within housing 602. Alternatively, the controller may be disposed in another device, housing, or module that is separate from module 600 (e.g., a wearable device, a laptop computer, a smartphone, a tablet computer, etc.) and communicatively coupled with light sources 804 by a wired or wireless communication link.

FIG. 9 shows module 600 as worn by a user. A distal end of light guide 808 is in physical contact with a surface 902 of a body 904 of the user. Surface 902 presses the light guide 1004 toward upper surface 614. Spring member 812 pushes light guide 808 in the opposite direction, thereby maintaining the distal end of light guide 808 in physical contact with surface 902 regardless of the topography and geometry of surface 902, and while one or more light-receiving members protruding from upper surface 614 (e.g., light-receiving members 606) are also in physical contact with surface 902. Light 814 emitted by light sources 804 enters body 904 and is scattered by a target within body 904. At least a portion of the scattered light returns toward module 600 and may be received by one or more light-receiving members 606 included in module 600. Light-receiving members 606 may be included in one or more detector assemblies included in module 600, as will now be described.

In the example shown in FIGS. 8 and 9, module 600 may be included in a time domain-based optical measurement system, such as a system based on TD-NIRS. In conventional configurations of an optical measurement system based on time domain techniques, a user may wear a module that emits light (e.g., NIR) to the user's body and collects the emitted light that has been scattered by tissue in the body. However, in the conventional configurations the detector is located away from the user so that the collected light must be conveyed from the wearable module to the detector by a long optical fiber. This creates several problems. First, when the wearable module is worn on a head of the user it is difficult for the distal end of light-collecting optical fibers to penetrate through the user's hair and maintain physical contact with the user's skin. Second, optical measurement systems that have many detectors require many optical fibers. Third, as explained above, the weight of the optical fibers may cause the module to move and shift around on the user's head, thus causing motion artifacts in the detected signal. Fourth, the length of the optical fibers generates temporal dispersion in the detected signal (e.g., TPSF) because some photons of the collected light are internally reflected many more times within the long optical fibers than other photons due to their different angle-of-incidence on the distal end of the optical fibers. In time domain-based systems, the variation in the time-of-flight of photons affects the TPSF and masks tissue response to the emitted light.

Figure 10:
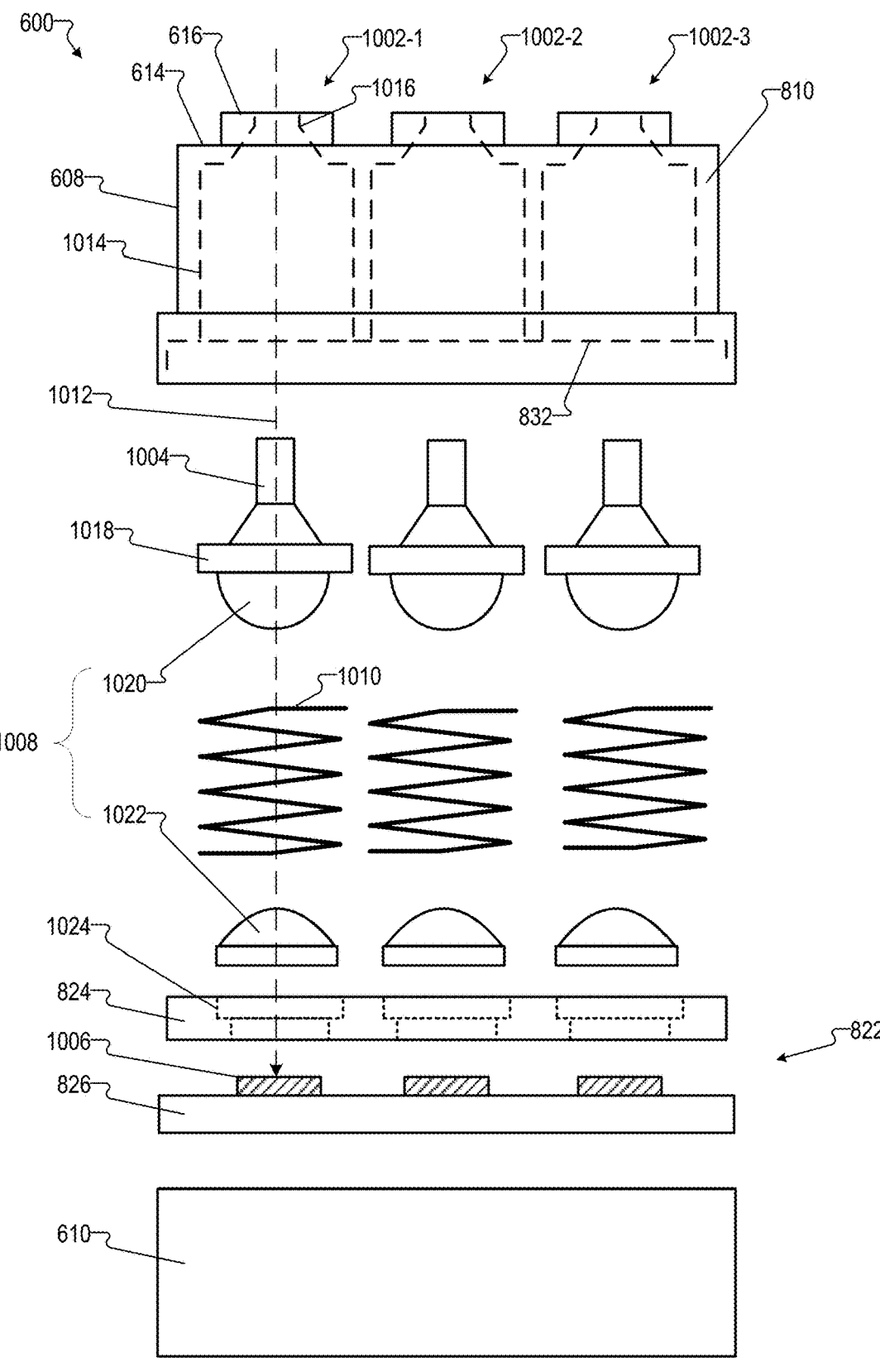
FIGS. 10 and 11 illustrate cross-sectional views of the module of FIGS. 6A-7B, including an exemplary detector assembly included in the wearable module, taken along the dashed line labeled X-X in FIG. 7A.
Figure 11:
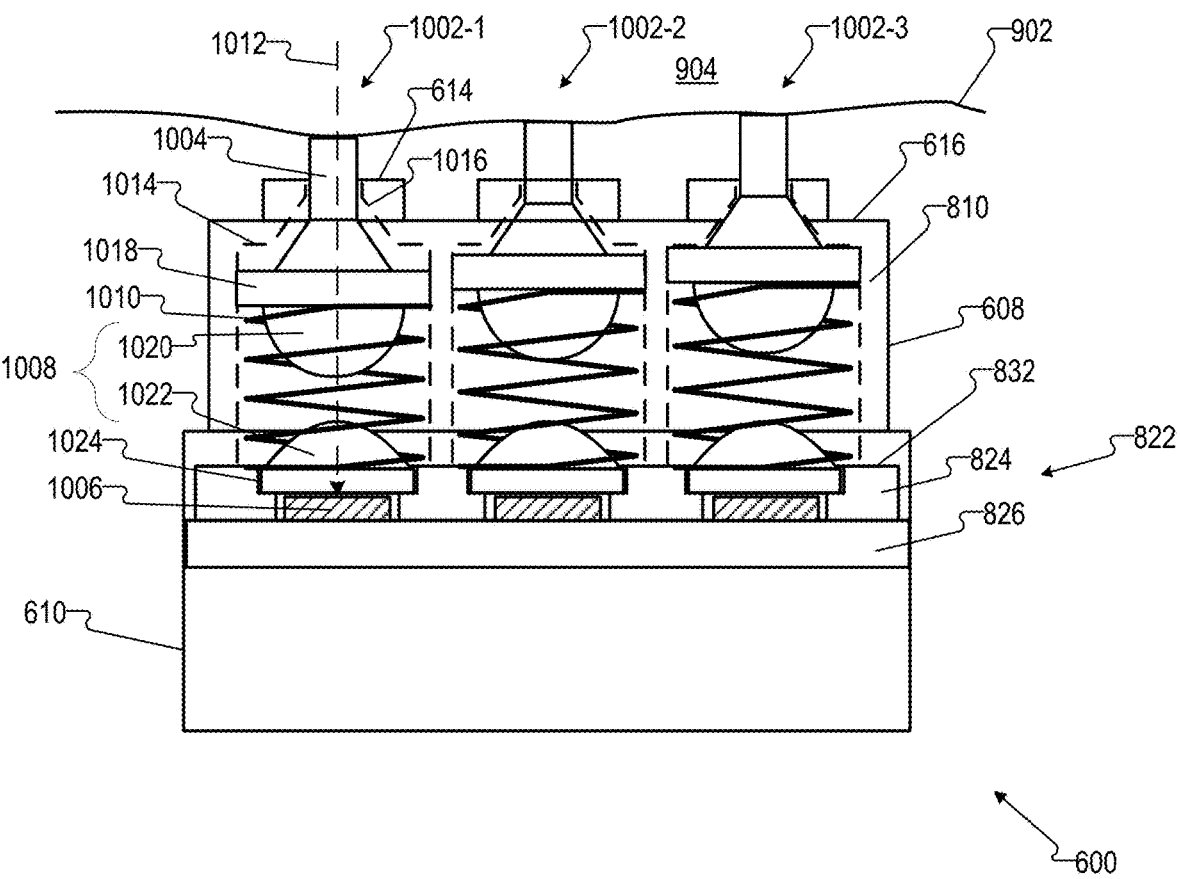

To address these issues, module 600, when used in a time domain-based optical measurement system, may include a plurality of detector assemblies, as will now be explained with reference to FIGS. 10 and 11. FIGS. 10 and 11 show a cross-sectional view of module 600, including exemplary detector assemblies included in module 600, taken along the dashed line labeled X-X shown in FIG. 7A. FIG. 10 shows an exploded view of module 600, and FIG. 11 shows a view of module 600 in an assembled state as worn by a user. As shown in FIGS. 10 and 11, module 600 includes a plurality of detector assemblies housed within housing 602. Module 600 may also include any other suitable components that are not shown in FIGS. 10 and 11, such as light source assembly 802 described above.

Each light-receiving member 606 (see FIGS. 6A-7B) in module 600 may be included in a distinct detector assembly 1002. FIGS. 10 and 11 show exemplary detector assemblies 1002-1, 1002-2, and 1002-3 corresponding to light-receiving members 606-1, 606-2, and 606-3, respectively. Detector assemblies corresponding to light-receiving members 606-4, 606-5, and 606-6 are also included in module 600 but are not shown in the cross-sectional view of FIGS. 10 and 11. Detector assembly 1002-1 will now be described. The following description applies equally to the other detector assemblies 1002 included in module 600.

As shown, detector assembly 1002 includes a light guide 1004 and a detector 1006. Detector assembly 1002 also includes a lens system 1008, light guide block 810, a spring member 1010, and support assembly 822, but one or more of these components may be omitted in other embodiments.

Light guide 1004 is configured to receive light scattered by the target ("light 1012") and guide light 1012 (e.g., photons) toward detector 1006. Light guide 1004 may be implemented by any suitable optical conduit described herein. As shown in FIGS. 10 and 11, light guide 1004 comprises a rigid, elongate waveguide. In alternative examples, light guide 1004 may comprise a bundle of optical fibers. In some examples, light guide 1004 implements optical conduit 116 to receive and guide light 124. A distal end portion of light guide 1004 is configured to protrude from upper surface 614 of upper housing 608 and receive light 1012 from the target. A proximal end portion of light guide 1004 is positioned near detector 1006 and emits light 1012 toward detector 1006.

Light guide 1004 may be supported within module 600 in any suitable way. In some examples, as shown in FIGS. 10 and 11, light guide 1004 is supported by light guide block 810 and spring member 1010. Light guide block 810 has a chamber 1014 in which light guide 1004 and spring member 1010 are positioned. A proximal end of chamber 1014 opens to the exterior of module 600 through an opening 1016 in upper surface 614 and frame support 616. Light guide 1004 is positioned within chamber 1014 such that the distal end portion of light guide 1004 is configured to protrude from upper surface 614 through opening 1016. The distal end portion of light guide 1004 protruding through opening 1016 forms light-receiving member 606-1.

In some examples, light guide 1004 is supported in a light guide block that is separate from light guide block 810. For example, light guide 1004 may be supported in a light guide block formed separately from upper housing 608 but that is mounted inside upper housing 608 and/or within another chamber (not shown) of light guide block 810.

As shown in FIGS. 10 and 11, support assembly 822 (e.g., first plate 824 and/or second plate 826) may be positioned over a distal end portion of light guide block 810 to hold light guide 1004 and spring member 1010 within chamber 1014.

In some examples, light guide 1004 is configured to move within chamber 1014 along an optical axis of light guide 1004 (e.g., a longitudinal direction of chamber 1014, which is a direction extending from the proximal end of chamber 1014 to the distal end of chamber 1014). Thus, the extent to which the distal end portion of light guide 1004 protrudes from upper surface 614 can be adjusted in order to maintain light guide 1004 in physical contact with the user's body.

Spring member 1010 is configured to bias the distal end portion of light guide 1004 away from upper surface 614. Thus, when module 600 is worn by a user, spring member 1010 biases the distal end portion of light guide 1004 toward a surface of the user's body, thereby helping to ensure that the distal end portion of light guide 1004 is in physical contact with the surface of the body. Spring member 1010 may bias the distal end portion of light guide 1004 away from upper surface 614 in any suitable way.

In some examples, as shown in FIGS. 10 and 11, spring member 1010 comprises a coil spring that wraps around an external surface of light guide 1004. A proximal end of spring member 1010 pushes against first plate 824, while the distal end of spring member 1010 pushes against a flange portion 1018 protruding from a portion of light guide 1004. Flange portion 1018 may be any suitable structure (e.g., a ring) attached to or protruding from light guide 1004. In some examples, flange portion 1018 is formed integrally with light guide 1004. By pressing against flange portion 1018, spring member 1010 biases the distal end of light guide 1004 away from upper surface 614. In alternative embodiments, spring member 1010 may be disposed on an upper side of flange portion 1018 and configured to pull flange portion 1018 (and hence light guide 1004) toward the distal end of chamber 1014. While FIGS. 10 and 11 show a coil spring, spring member 1010 may be implemented by any other suitable device or mechanism configured to bias the distal end of light guide 1004 away from upper surface 614 and toward the user's body.

Flange portion 1018 has a width (e.g., diameter) approximately equal to a width (e.g., diameter) of chamber 1014 (with sufficient tolerance to enable movement of light guide 1004) to maintain a lateral position of light guide 1004 within chamber 1014. Similarly, opening 1016 in upper surface 614 and frame support 616 has a width (e.g., diameter) approximately equal to a width (e.g., diameter) of light guide 1004 (with sufficient tolerance to enable movement of light guide 1004) to maintain a lateral position of light guide 1004 within opening 1016. With this configuration, a proximal end of light guide 1004 may be maintained in optical alignment with detector 1006. In alternative examples, detector assembly 1002-1 does not include spring member 1010. For instance, chamber 1014 may be approximately the same width (e.g., diameter) as light guide 1004 and light guide 1004 may be immovably attached to light guide block 810 within chamber 1014.

To further maintain light guide 1004 in optical alignment with detector 1006, detector 1006 is mounted on support assembly 822 (e.g., on first plate 824 or second plate 826), and support assembly 822 is securely and immovably mounted within housing 602, thereby preventing movement of detector 1006 relative to light guide 1004.

To eliminate a lossy interface between light guide 1004 and detector 1006 while allowing light guide 1004 to move relative to detector 1006, detector assembly 1002-1 includes lens system 1008. Lens system 1008 includes a first lens 1020 and a second lens 1022. First lens 1020 is configured to collimate light 1012 within chamber 1014. In some examples, first lens 1020 is formed integrally with light guide 1004 and/or flange portion 1018, and thus moves within chamber 1014 as light guide 1004 moves (due to action of spring member 1010 and/or pushing by the user's body). As shown in FIGS. 10 and 11, first lens 1020 fits inside spring member 1010 and thus directs light through a center opening of spring member 1010 to second lens 1022.

Second lens 1022 is configured to focus light 1012 onto detector 1006. Second lens 1022 is supported on first plate 824. Second lens 1022 may be supported on first plate 824 in any suitable way. As shown, second lens 1022 is positioned within a recess 1024 in first plate 824, thereby maintaining the position of second lens 1022 fixed relative to first lens 1020. In some embodiments, first plate 824 may be transparent (e.g., formed of glass), and second lens 1022 may be affixed to first plate 824 by a transparent adhesive. In yet other embodiments, second lens 1022 is formed integrally with an optically transparent first plate 824. Detector 1006 is mounted on second plate 826 in an optical path of light 1012. Thus, second lens 1022 focuses light 1012 onto detector 1006. With this configuration of lens system 1008, light 1012 at the proximal end of light guide 1004 is imaged onto detector 1006, thereby eliminating a lossy interface between light guide 1004 and detector 1006.

Detector 1006 may be implemented by any suitable detector described herein (e.g., detector 104, photodetector 106, etc.). In embodiments in which module 600 is configured for use in a time domain-based optical measurement system, detector 1006 may include at least one time-resolved single photon photodetector configured to detect photons from at least one light pulse after the at least one light pulse is scattered by the target. In some examples, detector 1006 comprises a plurality of SPAD circuits (e.g., an array of SPAD circuits 202).

In some examples, other circuitry associated with detector 1006 may also be included in module 600 (e.g., housed within housing 602). For instance, any one or more components of detector architecture 200 (e.g., control circuit 204, TDC 206, and/or signal processing circuit 208) may be housed, partially or entirely, within housing 602. These components may, for example, be disposed on support assembly 822 (e.g., first plate 824 and/or second plate 826) and/or light source plate 816. Additionally or alternatively, any one or more components of detector architecture 200 may be housed, partially or entirely, within an additional housing of another device that is separate from but communicatively coupled with module 600 (e.g., with detector 1006) by a wired or wireless communication link. The other device may be another wearable device or a non-wearable device.

FIG. 11 shows module 600 as worn by a user. A distal end of each light guide 1004 (e.g., light guide 1004-1 through 1004-3) is in physical contact with surface 902 of body 904 of the user. Surface 902 presses the light guide 1004 toward upper surface 614. Spring member 1010 pushes light guide 1004 in the opposite direction, thereby maintaining the distal end of each light guide 1004 in physical contact with surface 902 regardless of the topography and geometry of surface 902, and regardless of movement by the user, even when light guide 808 is also in physical contact with surface 902. With this configuration, scattered light 1012 from the target is received by light guides 1004 and directed to detector 1006. Moreover, maintaining the distal end of each light guide 1004 in physical contact with surface 902 prevents ambient light from entering light guide 1004 and corrupting the detected signal.

In the configurations just described, light guides 1004 may have a total length of about 10 millimeters (mm) or less, about 5 mm of less, or even 3 mm or less. As a result, the total distance a photon travels from the distal end portion of light guide 1004 to detector 1006 may be approximately 50 mm or less, 40 mm or less, or even 30 mm or less. Such short distances practically eliminates, or renders negligible, any temporal dispersion in the detected signal.

The non-invasive, wearable optical measurement systems described herein may detect biological information, including the dynamics of cerebral changes in [HbO2], [HHb], and [oxCCO], and neural activity in-vivo. Furthermore, the non-invasive, wearable optical measurement systems may also measure absolute optical properties of tissue, such as the absolute value of the reduced scattering coefficient $\mu_s'$ of the target, an absolute value of the absorption coefficient $\mu_a$ of the target, and/or the absolute pathlength of the photons through the target. To accurately measure these absolute properties, the optical measurements systems described herein are configured to accurately determine when a light pulse enters a user's body (e.g., the head). The time when the light pulse enters the user's body is subsequent to when the light source (e.g., light source 110) is activated to emit the pulse because there is a time delay between when an ON signal configured to activate the light source is received by the light source (e.g., light source 110) and when the actual emission of the light pulse by the light source occurs. This delay is caused, for example, because receipt of the ON signal from the controller is followed by a build-up of sufficient charge in the light source (e.g., a laser diode) to make the current that generates the light pulse.

Figure 12:
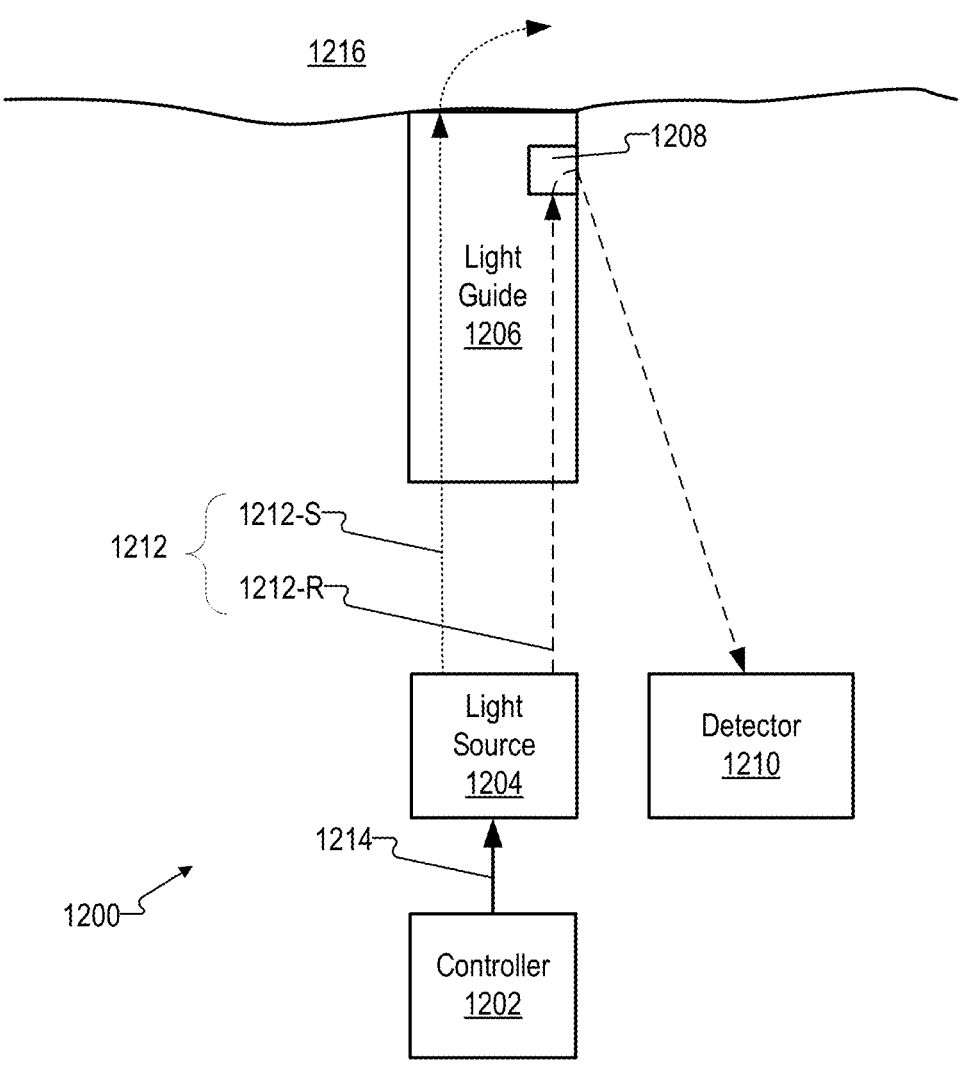
FIG. 12 illustrates an exemplary configuration of an optical measurement system configured to determine when a light pulse enters a body of a user and determine absolute optical properties of the target within the body.

FIG. 12 illustrates an exemplary configuration of an optical measurement system 1200 configured to determine when a light pulse enters a body of a user and to determine one or more optical properties of the target within the body. Optical measurement system 1200 may be implemented by any optical measurement system described herein (e.g., optical measurement system 100). As shown, optical measurement system 1200 includes a controller 1202, a light source 1204, a light guide 1206, a light diverter 1208, and a detector 1210. Optical measurement system 1200 may include any additional or alternative components as may suit a particular implementation.

Controller 1202 is configured to control light source 1204 to emit a light pulse 1212 having a short pulse width (e.g., 10-2000 ps). In some examples, controller 1202 is implemented by controller 112. Controller 1202 may control light source 1204 by transmitting a control signal 1214 to light source 1204 to turn light source 1204 ON and/or OFF, to set a pulse width of light pulse 1212, and/or to set an intensity of light pulse 1212.

Light source 1204 may be implemented by any suitable light source described herein (e.g., light source 110, light sources 804, etc.). In response to receiving control signal 1214 from controller 1202, light source 1204 may generate and emit light pulse 1212. Light pulse 1212 includes signal photons 1212-S and reference photons 1212-R. As will be explained below in more detail, signal photons 1212-S enter a body 1216 of a user while reference photons 1212-R are diverted and guided to detector 1210 without entering body 1216. While FIG. 12 represents signal photons 1212-S and reference photons 1212-R with separate dashed lines, in actuality light pulse 1212 comprises a single substantially coherent laser beam.

Light guide 1206 receives light pulse 1212 emitted by light source 1204. Light guide 1206 may be implemented by any suitable light guide described herein (e.g., optical conduit 114, light guide 606, light guide 808, etc.). Due to beam divergence of the emitted light pulse 1212, light guide 1206 guides signal photons 1212-S toward body 1216 (e.g., toward a target within body 1216) by total internal reflection of signal photons 1212-S within light guide 1206. Signal photons 1212-S exit a distal end of light guide 1206 and enter body 1216 where signal photons 1212-S may be absorbed and/or scattered by a target (e.g., brain tissue) within body 1216. A portion of signal photons 1212-S scattered by the target may then be detected by a photodetector (e.g., by detector 1210 and/or by another photodetector), which may output a signal representative of the light-pulse response of the target (e.g., a TPSF).

Light diverter 1208 is configured to divert reference photons 1212-R included in light pulse 1212 away from signal photons 1212-S and toward detector 1210 without reference photons 1212-R entering body 1216 or being scattered by the target within body 1216. Light diverter 1208 may divert reference photons 1212-R in any suitable way, as will now be explained.

Figure 13A:
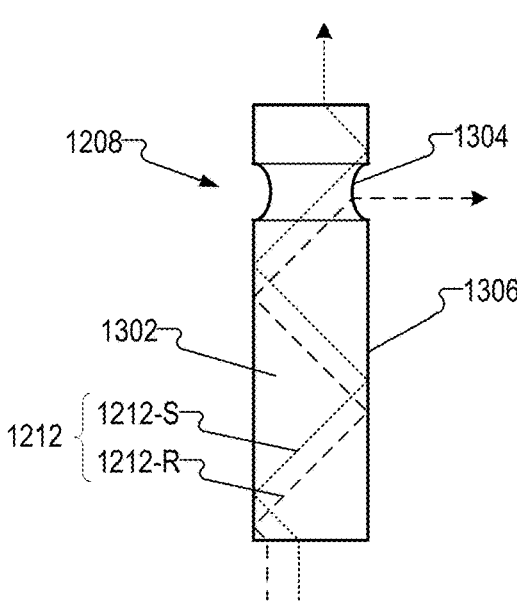
FIGS. 13A and 13B illustrate exemplary implementations of a light guide included in the optical measurement system of FIG. 12.
Figure 13B:
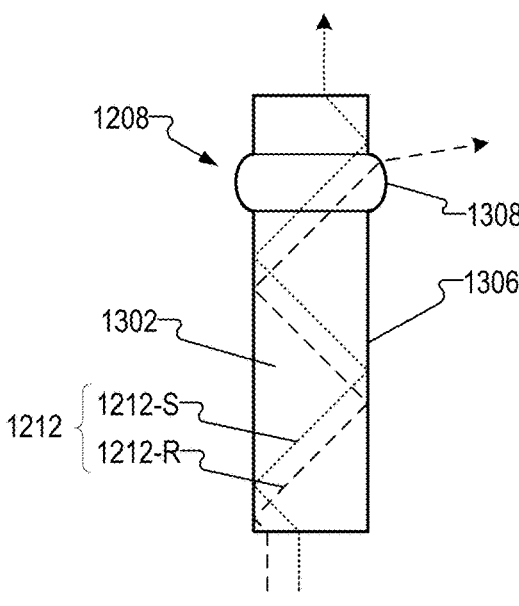

In some embodiments, light diverter 1208 is integrally formed with light guide 1206, as illustrated in FIGS. 13A and 13B. FIGS. 13A and 13B illustrate a side view (e.g., a view along a direction orthogonal to an optical axis) of an exemplary implementation of light guide 1206. As shown in FIG. 13A, light guide 1206 comprises a single optical conduit 1302 configured to guide light pulse 1212 by total internal reflection. Light diverter 1208 comprises a notch 1304 formed in an outer surface 1306 of optical conduit 1302. Notch 1304 may have any suitable surface profile or shape (e.g., concave, square, etc.) as may serve a particular implementation. Due to beam divergence of the emitted light pulse 1212, a subset of photons included in the emitted light pulse 1212 (i.e., reference photons 1212-R) are incident on an internal surface of notch 1304, which interrupts the total internal reflection of reference photons 1212-R within optical conduit 1302 and diverts reference photons 1212-R out of optical conduit 1302.

FIG. 13B is the similar to FIG. 13A, except that in FIG. 13B, light diverter 1208 comprises a convex protrusion 1308 formed in the outer surface 1306 of optical conduit 1302. Like notch 1304, protrusion 1308 interrupts the total internal reflection of reference photons 1212-R within optical conduit 1302 and diverts reference photons 1212-R out of light guide 1206.

As shown in FIGS. 13A and 13B, light diverter 1208 (e.g., notch 1304 and protrusion 1308) extends around the entire circumference of optical conduit 1302. This facilitates diversion of reference photons 1212-R to a plurality of detectors 1210 that may be positioned around optical conduit 1302 (e.g., similar to the embodiments illustrated in FIGS. 6A and 7A). However, in other examples, notch 1304 or protrusion 1308 may be discontinuous. Additionally or alternatively, light diverter 1208 may comprise a plurality of small notches 1304 or protrusions 1308 positioned around the circumference of optical conduit 1302 at positions corresponding to the plurality of detectors 1210. In this way, the amount of signal photons 1212-S in light pulse 1212 can be maximized.

In additional or alternative embodiments, light diverter 1208 may include a plurality of notches or protrusions positioned at different positions along a longitudinal (e.g., optical) axis of optical conduit 1302. This may facilitate the diversion of at least some reference photons 1212-R to detector 1210 when detector 1210 and light diverter 1208 are movable along the longitudinal direction of optical conduit 1302 relative to one another (e.g., by action of spring member 812 and/or spring member 1010).

In the embodiments illustrated in FIGS. 13A and 13B, the integrated light diverter 1208 and light guide 1206 assembly eliminate the need to optically align light diverter 1208 with light source 1204, light guide 1206, and/or detector 1210. Furthermore, the integrated light diverter 1208 prevents misalignments of light diverter 1208 during operation and use of optical measurement system 1200. It will be understood that light diverter 1208 can be positioned at any suitable location along a longitudinal direction of light guide 1206 as may serve a particular implementation.

Figure 14:
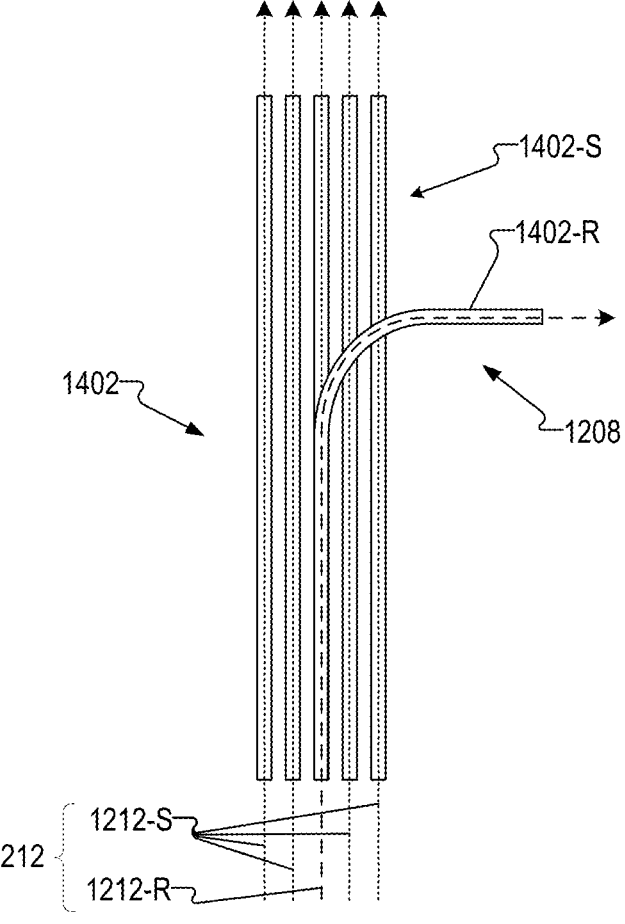
FIG. 14 illustrates another exemplary implementation of a light guide included in the optical measurement system of FIG. 12.

FIG. 14 illustrates an alternative embodiment in which light guide 1206 comprises a plurality of optical fibers 1402, each of which separately receives photons included in light pulse 1212. A group of optical fibers 1402-S receive and guide signal photons 1212-S toward body 1216 (not shown in FIG. 14), while one or more other optical fibers 1402-R that bend or extend away from fibers 1402-S receive reference photons 1212-R and guide reference photons 1212-R toward detector 1210 (not shown in FIG. 14) without reference photons 1212-R) entering body 1216.

Figure 15:
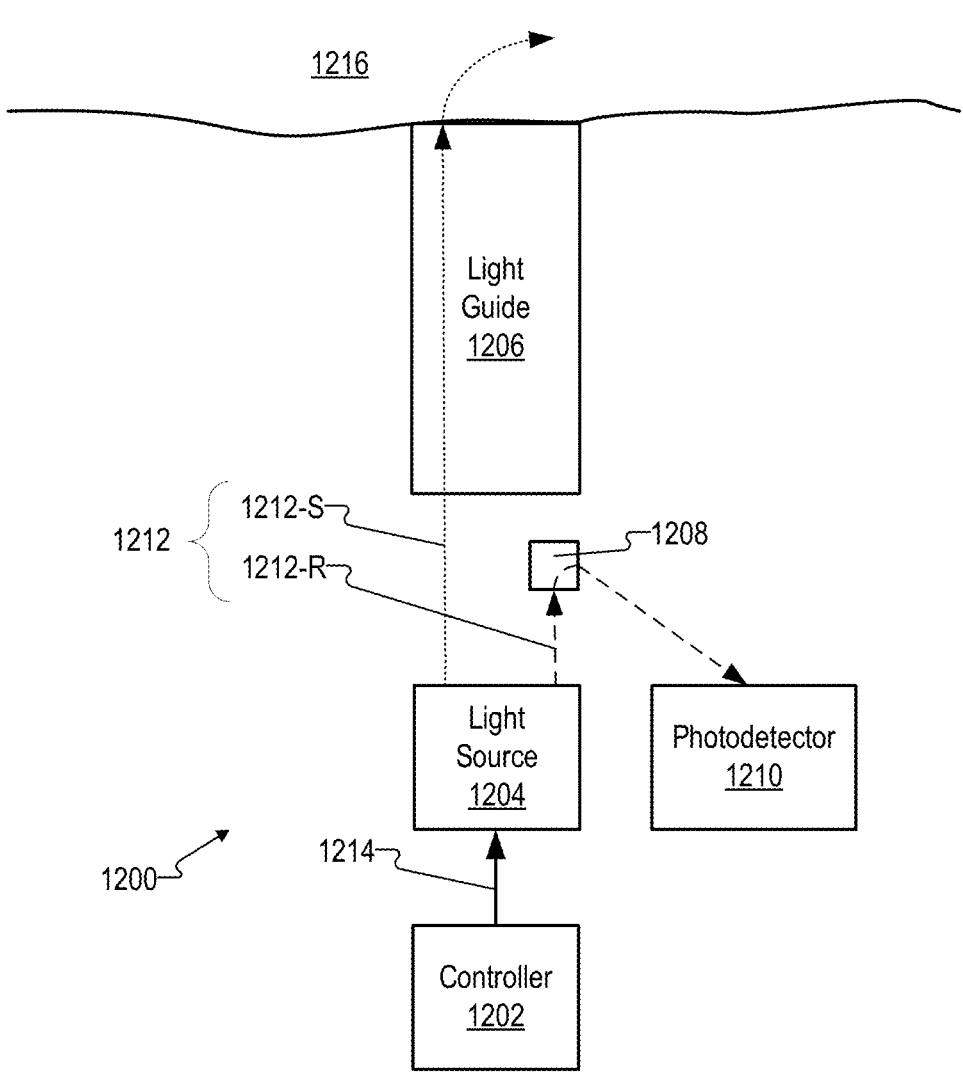
FIG. 15 illustrates another exemplary configuration of the optical measurement system of FIG. 12.

In some embodiments, light diverter 1208 is separate from light guide 1206, as illustrated in FIG. 15. FIG. 15 is similar to FIG. 12, except that in FIG. 15, light diverter 1208 is located between light source 1204 and light guide 1206 to thereby divert reference photons 1212-R before reference photons 1212-R enter into light guide 1206. In these embodiments, light diverter 1208 may be implemented by any suitable optical element, such as a mirror, a diffractive optical element, a light guide (e.g., an optical fiber), etc. Light diverter 1208 may be positioned such that signal photons 1212-S are not incident on light diverter 1208.

In alternative embodiments, signal photons 1212-S may transmit through light diverter 1208 while reference photons 1212-R may be selectively diverted by light diverter 1208. This may be accomplished, for example, by incorporating two different wavelengths (e.g., from two different laser diodes) into light pulse 1212 and selectively filtering (e.g., with a bandpass filter) photons in the first wavelength as signal photons 1212-S and selectively diverting photons in the second wavelength (e.g., by way of a mirror behind the filter). Alternatively, selective filtering may be based on differently polarized light in a single wavelength.

Alternatively to positioning light diverter 1208 between light source 1204 and light guide 1206, light diverter 1208 may instead be positioned between light guide 1206 and body 1216 (e.g., at a distal end of light guide 1206).

Referring again to FIG. 12 and as mentioned above, light diverter 1208 is configured to divert reference photons 1212-R toward detector 1210. Reference photons 1212-R may be diverted toward detector 1210 in any suitable way. In some examples, light diverter 1208 may be configured to redirect reference photons 1212-R directly to detector 1210 (e.g., without any intervening optical elements). Alternatively, light diverter may be configured to redirect reference photons 1212-R indirectly to detector 1210, such as by way of one or more intervening optical elements (e.g., lenses, light guides, optical conduits, mirrors, diffraction optical elements, etc.). In some examples, the one or more intervening optical elements may be included in a detector assembly (e.g., a detector assembly 1002) configured to receive signal photons 1212-S after the signal photons 1212-S have been scattered by the target and guide the signal photons 1212-S to detector 1210.

In some examples, an optical pathlength of the signal photons from the light diverter to a distal end of the light guide is approximately 50 mm or less, approximately 40 mm or less, or even approximately 30 mm or less. As a result, the reference photons 1212-R are may be detected practically instantaneously with entrance of signal photons 1212-S into body 1216. In additional or alternative embodiments, an optical pathlength of reference photons 1212-R detected by detector 1210 is less than an optical pathlength of signal photons 1212-S detected by detector 1210.

Figure 16:
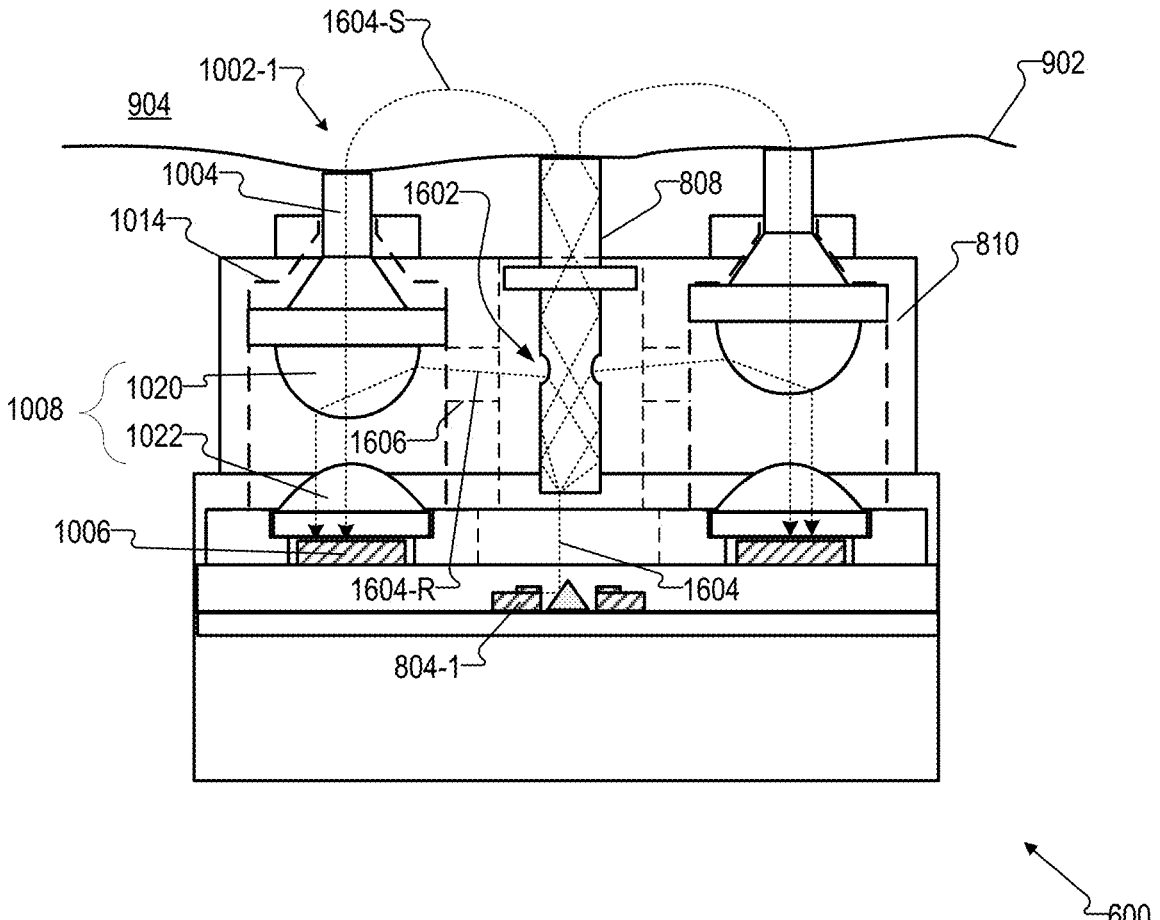
FIG. 16 illustrates a cross-sectional view of an exemplary implementation of the wearable module of FIG. 7A, as taken along the line XVI-XVI in FIG. 7A, of the optical measurement system of FIG. 12.

FIG. 16 illustrates an exemplary implementation of optical measurement system 1200. FIG. 16 also shows a cross-sectional view of an exemplary implementation of wearable module 600 as taken along the line XVI-XVI in FIG. 7A. (Spring members 812 and 1010 are not shown in FIG. 16, to enable easier viewing of other features.) In FIG. 16, wearable module 600 is the same as wearable module 600 depicted in FIGS. 6A-11 except that, in FIG. 16, wearable module 600 includes a light diverter 1602 configured to divert reference photons 1604-R toward detectors 1006. Reference photons 1604-R are included in a light pulse 1604 emitted by light source 804-1. As shown, light diverter 1602 is in the form of a notch formed in an outer surface of light-emitting light guide 808, although light diverter 1602 may have any other suitable form. A hole or slit 1606 is formed in light guide block 810 between chamber 818 and chamber 1014 to allow reference photons 1604-R to travel from light-emitting light guide 808 to detector assembly 1002-1. Reference photons 1604-R are directed to lens system 1008 (e.g., to first lens 1020 of detector assembly 1002-1 and then to second lens 1022). Lens system 1008 directs reference photons 1604-R to detector 1006.

Light pulse 1604 also includes signal photons 1604-S, which are received by light-emitting light guide 808 and guided by total internal reflection to a target within body 904. A portion of signal photons 1604-S are scattered by the target and collected by detector assembly 1002-1 and guided to detector 1006 by way of light-receiving light guide 1004 and lens system 1008 (e.g., first lens 1020 and second lens 1022).

With the configuration illustrated in FIG. 16, no additional components or optical elements are needed to divert reference photons 1604-R to detector 1006 without entering or being scattered by the target. Such configuration does not take any additional space within wearable module 600, and does not require alignment of additional optical components.

It will be recognized that FIG. 16 is merely exemplary, as wearable module 600 may be modified in any suitable way. For example, light diverter 1602 may direct reference photons directly to second lens 1022 rather than first lens 1020. Additionally or alternatively, wearable module 600 may be modified to accommodate any suitable configuration of light diverter 1602.

Figure 17:
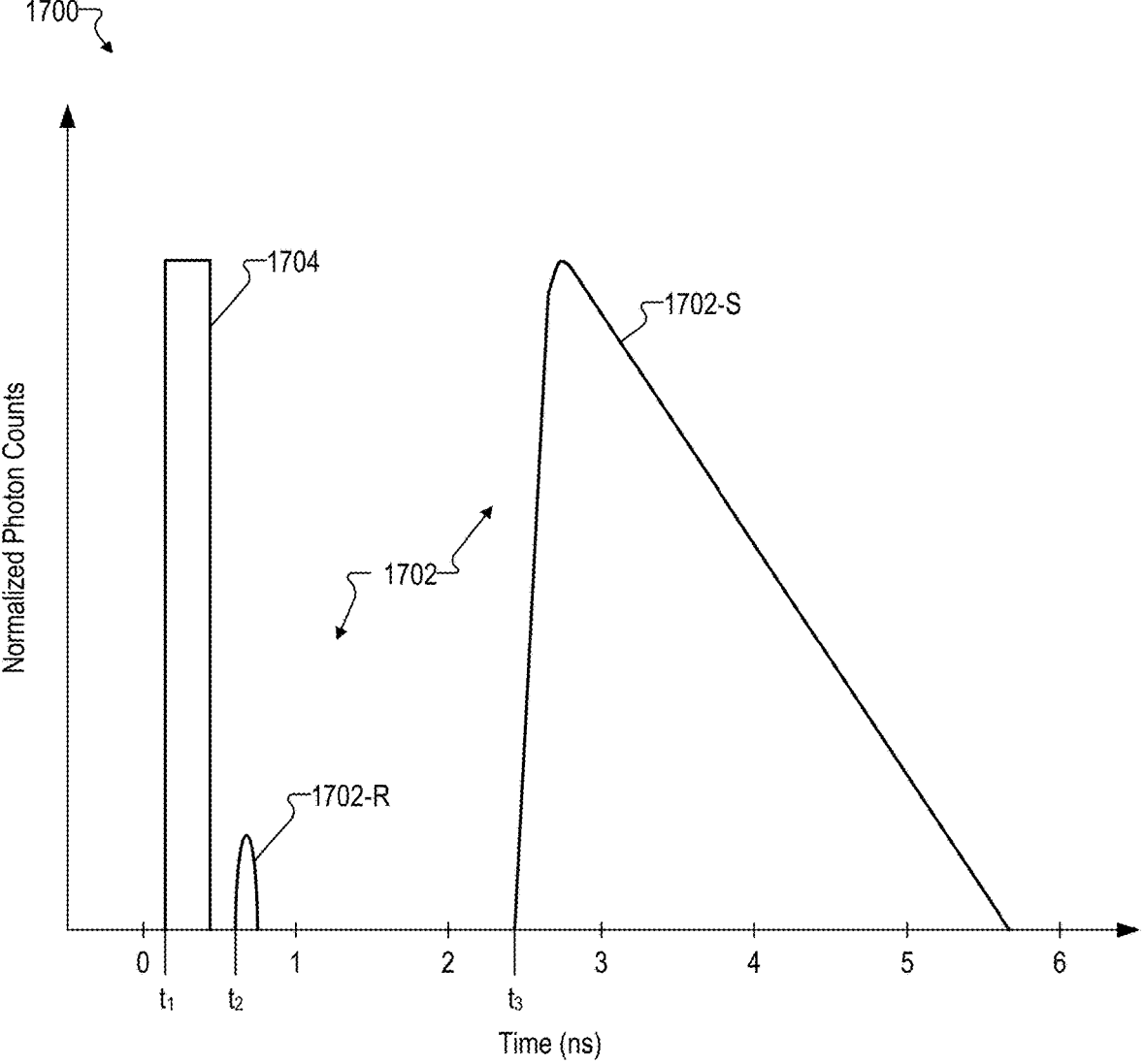
FIG. 17 illustrates a graph of an exemplary histogram that may be generated by the optical measurement system of FIG. 12.

Operation of optical measurement system 1200 will now be described with reference to FIG. 12 and FIG. 17. FIG. 17 illustrates a graph 1700 of an exemplary histogram 1702 that may be generated by optical measurement system 1200 in response to light pulse 1212 (which, in practice, represents a plurality of light pulses) and that indicates a temporal distribution of photons (reference photons 1212-R and signal photons 1212-S) detected by detector 1210. Graph 1700 shows a normalized count of photons on a y-axis and time bins on an x-axis. Graph 1700 also shows a pulse 1704 indicating a timing of control signal 1214 relative to histogram 1702, but it will be understood that pulse 1704 generally is not included in graph 1700 (e.g., in the histogram generated by optical measurement system 1200). Histogram 1702 may be generated in any suitable way.

As shown in graph 1700, controller 1202 sends control signal 1214 (represented by peak pulse 1704 in FIG. 17) to light source 1204 at time $t_1$ to generate and emit light pulse 1212. As mentioned above, due to the drive circuitry in light source 1204, there is a delay between the receipt of control signal 1214 and emission of light pulse 1212. Therefore, the timing of control signal 1214 cannot be used to determine when light pulse 1212 was emitted and entered body 1216.

However, detector 1210 detects reference photons 1212-R after reference photons 1212-R are diverted from light pulse 1212 without entering body 1216 or being scattered by the target. Based on the detection of reference photons 1212-R, optical measurement system 1200 may determine a temporal distribution of reference photons 1212-R, represented by reference peak 1702-R first appearing at time $t_2$. Due to the scattering of signal photons 1212-S within body 1216, a temporal distribution of signal photons detected by detector 1210, represented by signal peak 1702-S(a TPSF), does not appear until time $t_3$, some time after time $t_2$. However, because the reference photons 1212-R have not been slowed by scattering within body 1216, and because the optical path distance from light diverter 1208 to detector 1210 is short (e.g., on the order of a few tens of millimeters), the time $t_2$ at which reference photons 1212-R are detected by detector 1210 can be assumed to be the time when signal photons 1212-S in the same light pulse 1212 entered body 1216.

Thus, signal peak 1702-S can be shifted in time $t_0$ time $t_2$ to when reference photons 1212-R were detected.

Even if the optical pathlength of reference photons 1212-R is statistically significant (e.g., if detector 1210 is located off the wearable module at some distance), the optical pathlength of the reference photons 1212-R is known and can be used in conjunction with the speed of light to adjust or correct the location of reference peak 1702-R. Furthermore, because the optical pathlength of signal photons leaving body 1216 to detector 1210 is short (e.g., on the order of a few tens of millimeters), the time $t_3$ at which signal photons 1212-S are detected by detector 1210 can be assumed to be the time when signal photons 1212-S exited body 1216. Nevertheless, even if the optical pathlength of signal photons 1212-S exiting body 1216 to detector 1210 is statistically significant, such optical pathlength is known and can be used in conjunction with the speed of light to adjust or correct the location of signal peak 1702-S.

With the measurement data (e.g., histogram 1702) collected and/or generated by optical measurement system 1200 (e.g., by detector 1210 and/or by a processing unit communicatively coupled to detector 1210), optical measurement system 1200 (or any other computing system communicatively coupled with optical measurement system 1200) can determine the precise time when signal photons 1212-S entered body 1216. Thus, the measurement data can be used to determine the absolute optical pathlength of signal photons 1212-S through body 1216 (e.g., through the target within body 1216). Optical measurement system 1200 may determine when signal photons 1212-S entered body 1216 by measuring a time difference between an occurrence of a reference output pulse generated by the detector, as indicated by reference peak 1702-R, and a signal output pulse generated by detector 1210, as indicated by signal peak 1702-S. The reference output pulse indicates that detector 1210 has detected a reference photon 1212-R and the signal output pulse indicates that detector 1210 has detected a signal photon 1212-S.

The absolute optical pathlength through body 1216 can be used to determine the absolute concentration of oxCCO ([oxCCO]) present in the target because the Beer-Lambert law indicates that the attenuation of signal photons 1212-S due to CCO present in the target is related to the concentration of oxCCO in the target, its extinction coefficient (E), and the optical pathlength of signal photons 1212-S.

Additionally, optical measurement system 1200 may use the measurement data collected by optical measurement system 1200 to determine the absolute measures of the reduced scattering coefficient $\mu_s'$ and absorption coefficient $\mu_a$ of the target by fitting the measurement data with a standard model of diffusion theory (e.g., a non-linear fitting procedure based on the Levenberg-Marquardt approach). By determining the absolute measures of the reduced scattering coefficient $\mu_s'$ and absorption coefficient $\mu_a$ of the target and the absolute optical pathlength, optical measurement system 1200 may also determine the absolute concentrations of HbO2 ([HbO2]) and HHb ([HHb]) and the absolute tissue saturation (StO2) of the target. These absolute measures provide a baseline from which changes in [HbO2] and [HHb] may be measured, thereby providing accurate scaling of changes in [HbO2] and [HHb]. Knowing the accurate scaling of changes in [HbO2] and [HHb] also enables an appropriate solve of the modified Beer-Lambert equation, which leads to less crosstalk with hemoglobin when measuring the absolute concentration of oxCCO ([oxCCO]) and changes in [oxCCO], improved accuracy in measuring

[oxCCO], and a higher-fidelity [oxCCO] monitoring system over conventional NIRS methodologies.

In some examples, system noise can be removed and the signal-to-noise ratio increased by using the instrument response function of detector 1210 to deconvolve histogram 1702 before histogram 1702 is analyzed to determine the absolute measures of the reduced scattering coefficient $\mu_s'$ and absorption coefficient Ha of the target and the absolute optical pathlength. Additionally or alternatively, the signal-to-noise ratio can be increased by subtracting the dark count rate prior to the Beer-Lambert conversion.

In some examples, the magnitude of reference peak 1702-R can be used as a reference to monitor for fluctuations in the intensity of light pulses 1212 emitted by light source 1204. For example, variations in the detected intensity of reference peak 1702-R can be used to adjust or correct (e.g., normalize) signal peak 1702-S.

In the systems and apparatuses described above, the optical properties and neural activity of the tissue is measured by multiplexing two or more different wavelengths. For example, light source 1204 may be configured to emit a plurality of light pulses 1212 in a plurality (e.g., eight) different wavelengths (e.g., 685 nm, 780 nm, 798 nm, 804 nm, 828 nm, 834 nm, 840 nm, and 850 nm). During acquisition of measurement data, each multiplexed wavelength may be set with a certain integration time that will result in a repetition rate for each wavelength and the overall acquisition frequency, which is preferably in physiological ranges (e.g., less than or equal to 4 Hz). The histogram generated from each multiplexed wavelength may then be processed as described above to determine the absolute optical properties of the target for each multiplexed wavelength.

Figure 18A:
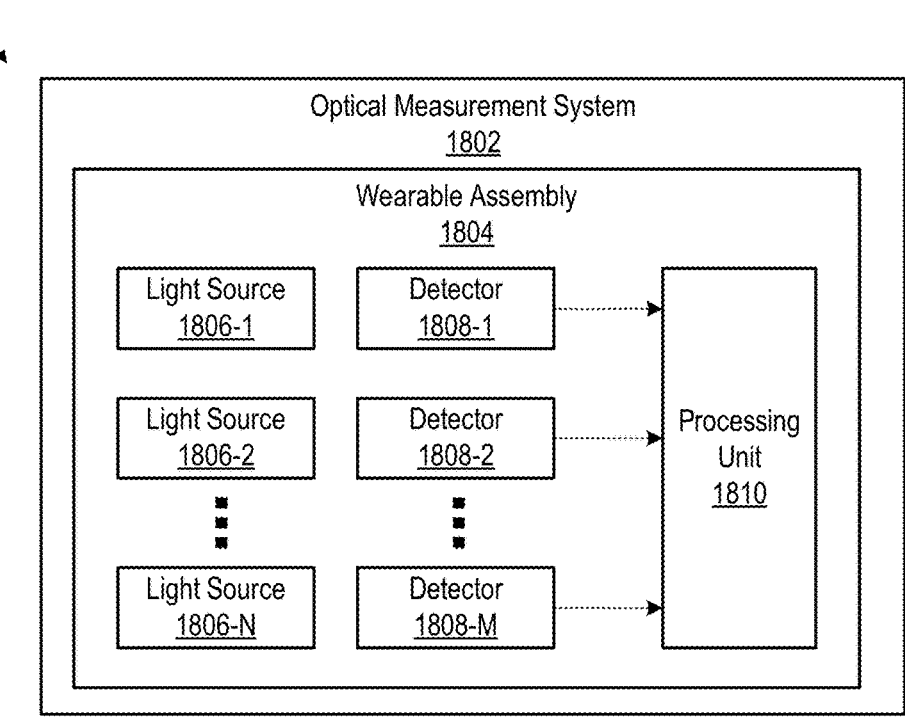
FIGS. 18A and 18B illustrate exemplary configurations of an exemplary optical measurement system that includes a processing unit.
Figure 18B:
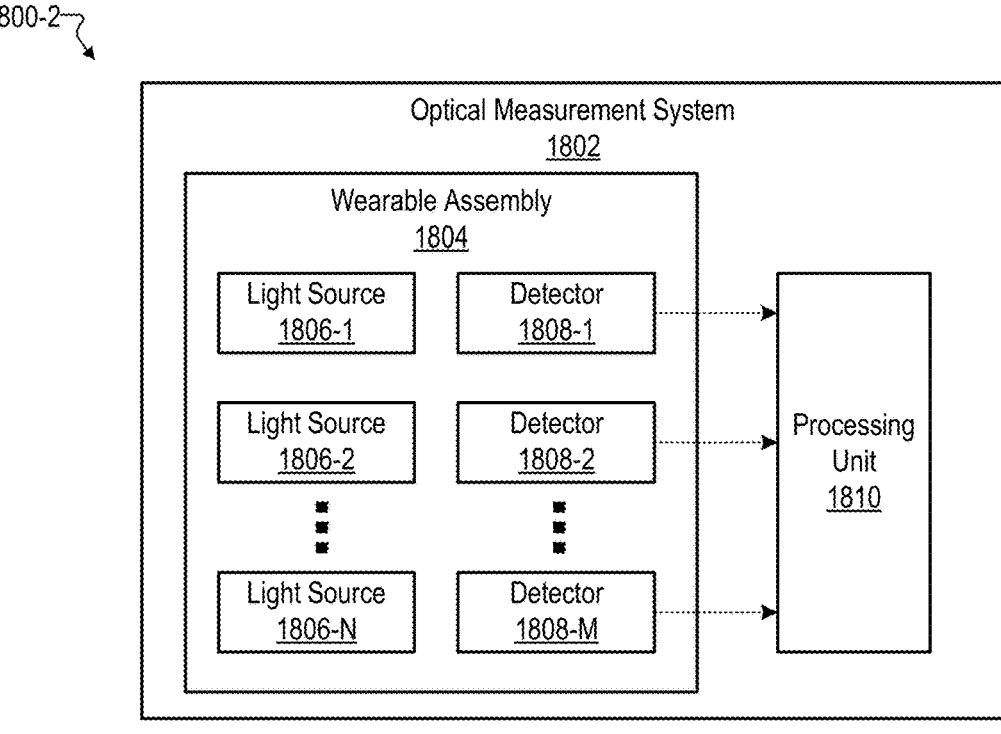

In some examples, the optical measurement systems described herein (e.g., optical measurement system 100 or optical measurement system 1200) may further include a processing unit configured to perform one or more operations based on arrival times detected by the detectors described herein. For example, FIGS. 18A-18B show illustrative configurations 1800-1 and 1800-2 of an exemplary optical measurement system 1802 in accordance with the principles described herein.

Optical measurement system 1802 may be an implementation of optical measurement system 100 or optical measurement system 1200 and, as shown, includes a wearable assembly 1804, which includes N light sources 1806 (e.g., light sources 1806-1 through 1806-N) and M detectors 1808 (e.g., detectors 1808-1 through 1808-M). Optical measurement system 1802 may include any of other components as may serve a particular implementation.

Wearable assembly 1804 may be implemented by any of the wearable devices, wearable modules, and/or wearable units described herein (e.g., wearable module 600). For example, wearable assembly 1804 may be implemented by a wearable device configured to be worn on a user's head. Wearable assembly 1804 may additionally or alternatively be configured to be worn on any other part of a user's body. In some examples, optical measurement system 1802 may include a plurality of wearable assemblies 1804.

Light sources 1806 are each configured to emit light and may be implemented by any of the light sources described herein. Detectors 1808 may each be configured to detect arrival times for photons of the light emitted by one or more light sources 1806 after the light is scattered by the target or diverted without being scattered by the target. For example, a detector 1808 may include a photodetector configured to generate a photodetector output pulse in response to detecting a photon of the light and a TDC configured to record a timestamp symbol in response to an occurrence of the photodetector output pulse, the timestamp symbol representative of an arrival time for the photon. Detectors 1808 may be implemented by any of the detectors described herein.

In configuration 1800-1, a processing unit 1810 is also included in wearable assembly 1804. In configuration 1800-2, processing unit 1810 is not included in wearable assembly 1804 (i.e., processing unit 1810 is located external to wearable assembly 1804). Either configuration 1800-1 or 1800-2 may be used in accordance with the systems, circuits, and methods described herein.

Detectors 1808 on wearable assembly 1804 may output signals representative of photon arrivals, as described herein. Processing unit 1810 is configured to receive the output signals and perform one or more operations based on the signals. For example, processing unit 1810 may generate measurement data (e.g., one or more histograms) based on the signals, as described herein.

As mentioned, in configuration 1800-2, processing unit 1810 is not included in wearable assembly 1804. For example, processing unit 1810 may be included in a wearable device separate from wearable assembly 1804. To illustrate, processing unit 1810 may be included in a wearable device configured to be worn off the head (e.g., on a belt) while wearable assembly 1804 is worn on the head. In these examples, one or more communication interfaces (e.g., cables, wireless interfaces, etc.) may be used to facilitate communication between wearable assembly 1804 and the separate wearable device.

Additionally or alternatively, in configuration 1800-2, processing unit 1810 may be remote from the user (i.e., not worn by the user). For example, processing unit 1810 may be implemented by a stand-alone computing device communicatively coupled to wearable assembly 1804 by way of one or more communication interfaces (e.g., cables, wireless interfaces, etc.).

In some examples, processing unit 1810 may be distributed between multiple devices and/or multiple locations as may serve a particular implementation. Processing unit 1810 may be implemented by processor 108, controller 112, control circuit 204, and/or any other suitable processing and/or computing device or circuit.

Figure 19:
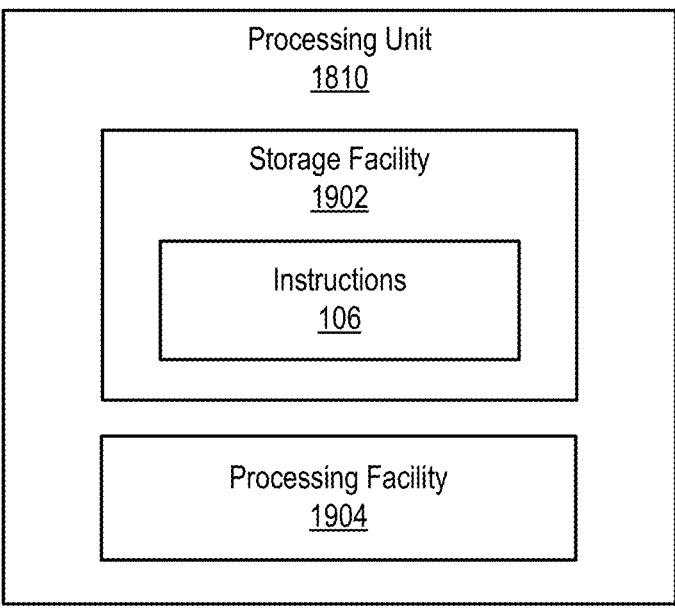
FIG. 19 illustrates an exemplary implementation of the processing unit of FIG. 18.

For example, FIG. 19 illustrates an exemplary implementation of processing unit 1810 in which processing unit 1810 includes a memory 1902 and a processor 1904 configured to be selectively and communicatively coupled to one another. In some examples, memory 1902 and processor 1904 may be distributed between multiple devices and/or multiple locations as may serve a particular implementation.

Memory 1902 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferroelectric random-access memory ("RAM"), and an optical disc. Exemplary volatile storage media include, but are not limited to, RAM (e.g., dynamic RAM).

Memory 1902 may maintain (e.g., store) executable data used by processor 1904 to perform one or more of the operations described herein. For example, memory 1902 may store instructions 1906 that may be executed by processor 1904 to perform any of the operations described herein. Instructions 1906 may be implemented by any suitable application, program (e.g., sound processing program), software, code, and/or other executable data instance. Memory 1902 may also maintain any data received, generated, managed, used, and/or transmitted by processor 1904.

Processor 1904 may be configured to perform (e.g., execute instructions 1906 stored in memory 1902 to perform) various operations described herein. For example, processor 1904 may be configured to perform any of the operations described herein as being performed by processing unit 1810.

For example, processing unit 1810 may be configured to determine a temporal distribution of signal photons 1212-S detected by detector 1210, determine a temporal distribution of reference photons 1212-R detected by detector 1210, and generate measurement data (e.g., histogram 1702) based on the temporal distribution of the signal photons 1212-S and the temporal distribution of the reference photons 1212-R. Processing unit 1810 may also be configured to determine, based on the temporal distribution of the reference photons 1212-R detected by detector 1210, when the signal photons 1212-S entered body 1216. Based on this information, processing unit 1810 may be configured to determine at least one of an absolute value of a reduced scattering coefficient $\mu_s'$ of the target, an absolute value of an absorption coefficient Ja of the target, and an absolute value of an absorption coefficient Ha of the target. Processing unit may also be configured to determine, based on the measurement data, an oxidation state of CCO present in the target (e.g., a concentration of oxCCO in the target).

FIGS. 20-25 illustrate embodiments of a wearable device 2000 that includes elements of the optical measurement systems described herein. In particular, the wearable devices 2000 include a plurality of modules 2002, similar to wearable module 600 shown in FIGS. 6A-7B, described herein. For example, each module 2002 includes a source (e.g., light-emitting member 604) and a plurality of detectors (e.g., light-receiving members 606-1 through 606-6). The source may be implemented by or be similar to one or more light sources or light source assemblies described herein (e.g., light source 110, light source assembly 802, etc.). Each detector may implement or be similar to one or more detectors or detector assemblies described herein (e.g., detector 104, detector 1210, etc.) and may include a plurality of photodetectors. The wearable devices 2000 may each also include a controller (e.g., controller 112) and a processor (e.g., processor 108) and/or be communicatively connected to a controller and/or a processor. In general, wearable device 2000 may be implemented by any suitable headgear and/or clothing article configured to be worn by a user. The headgear and/or clothing article may include batteries, cables, and/or other peripherals for the components of the optical measurement systems described herein. In some examples, the headgear includes one or more modules 600. Additionally or alternatively, modules 2002 are included in or implemented by modules 600.

Figure 20:
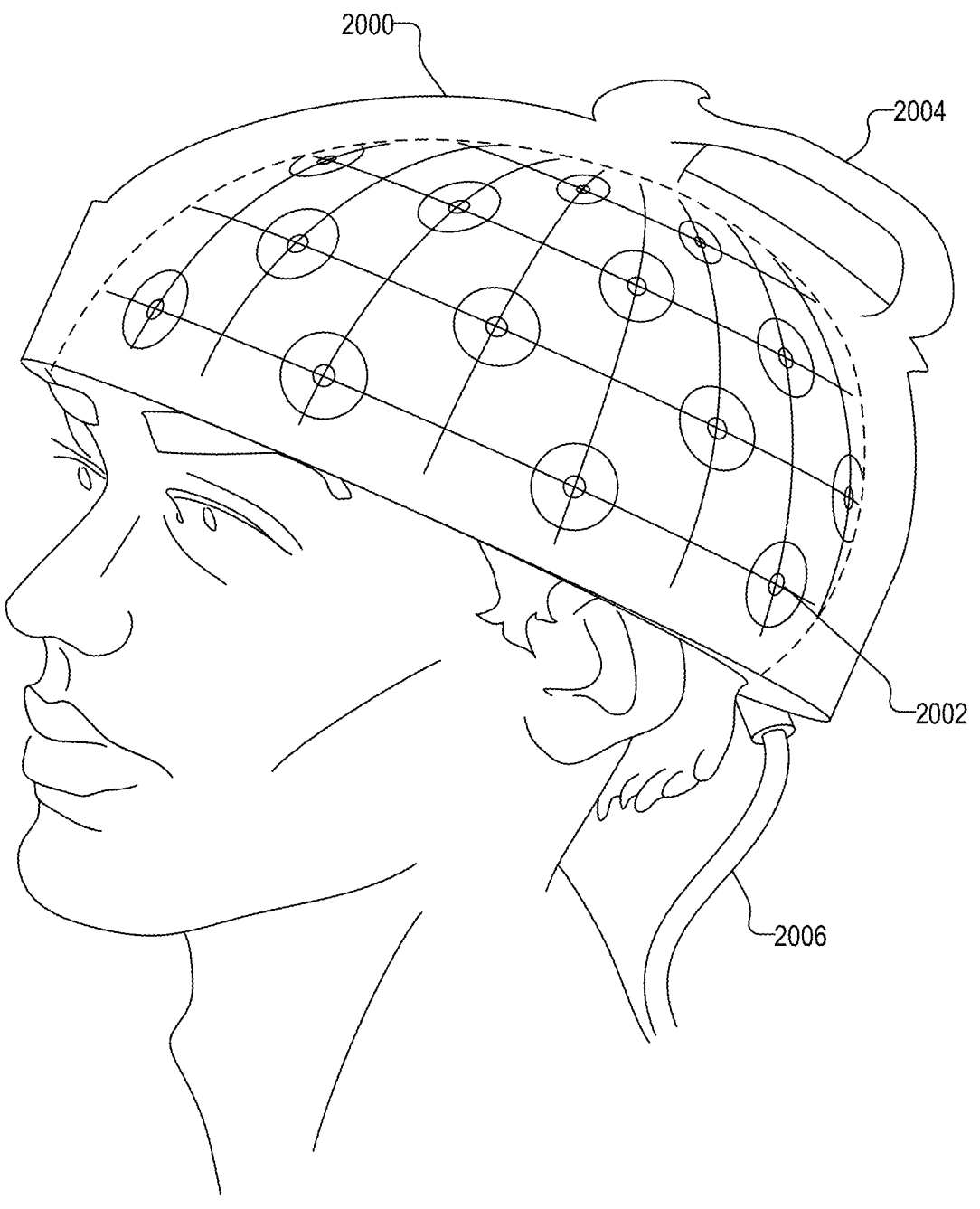
FIGS. 20-25 illustrate embodiments of a wearable device that includes elements of the optical detection systems described herein.
Figure 21:
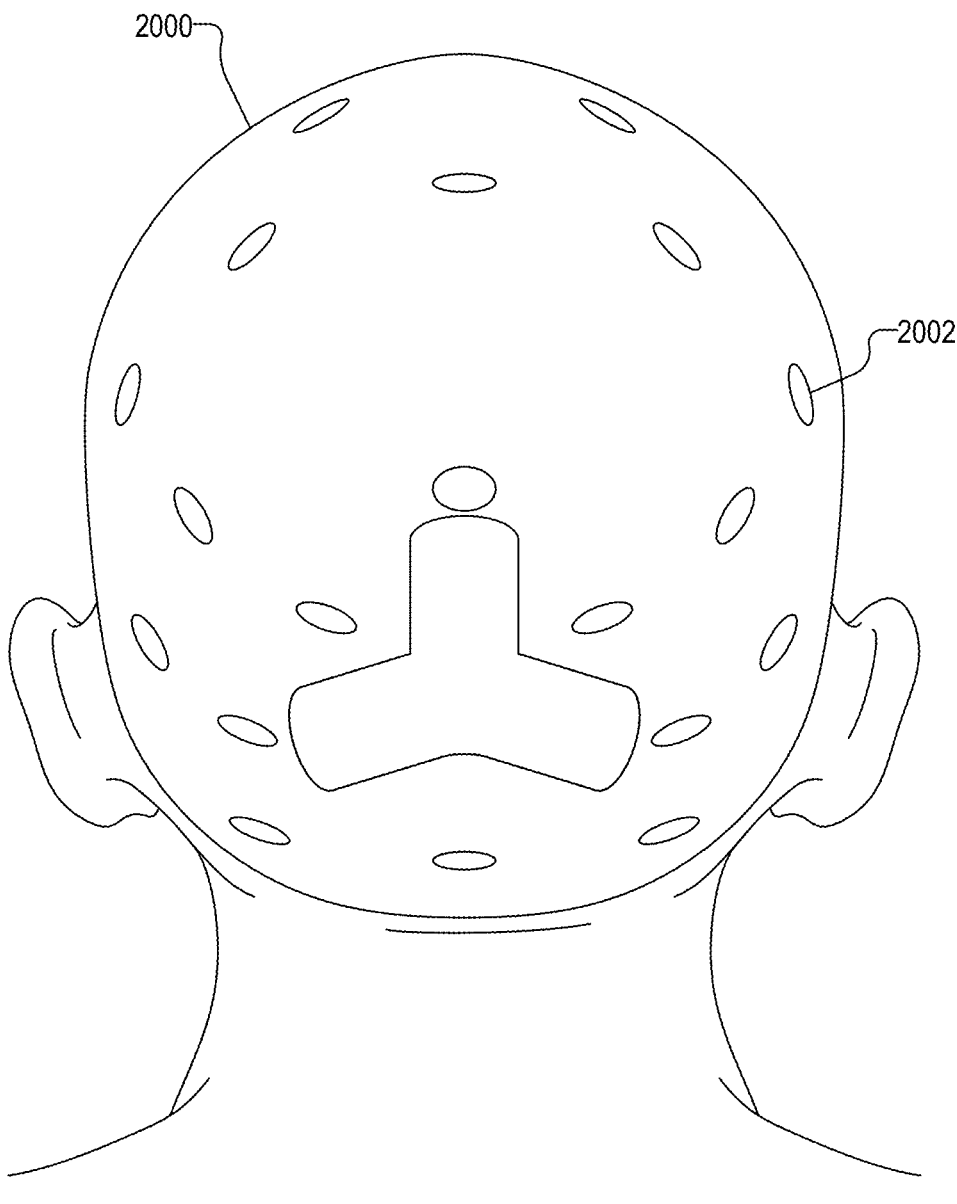
Figure 22:
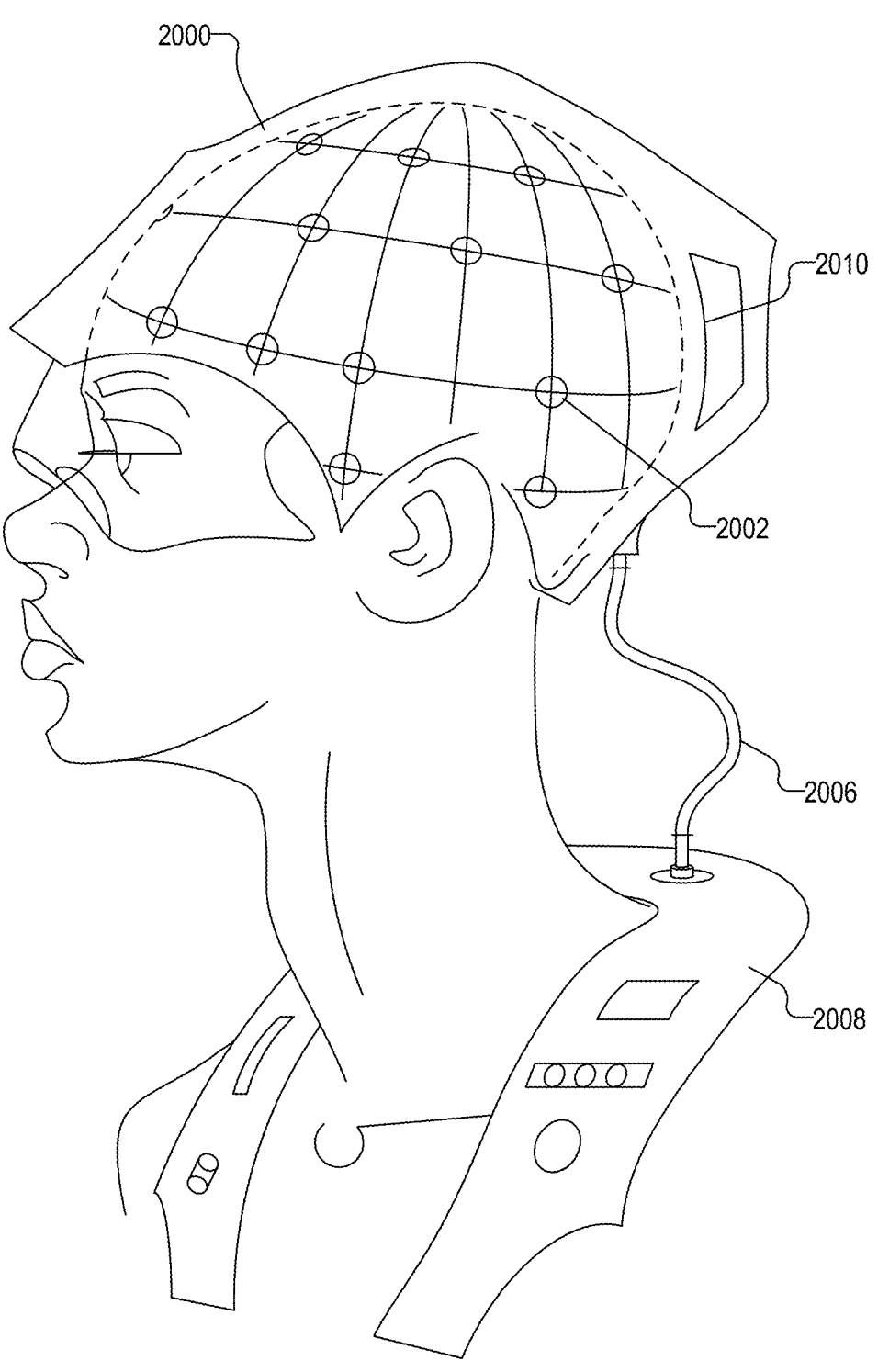

FIG. 20 illustrates an embodiment of a wearable device 2000 in the form of a helmet with a handle 2004. A cable 2006 extends from the wearable device 2000 for attachment to a battery or hub (with components such as a processor or the like). FIG. 21 illustrates another embodiment of a wearable device 2000 in the form of a helmet showing a back view. FIG. 22 illustrates a third embodiment of a wearable device 2000 in the form of a helmet with the cable 2006 leading to a wearable garment 2008 (such as a vest or partial vest) that can include a battery or a hub (e.g., processing unit 1810). Alternatively or additionally, the wearable device 2000 can include a crest 2010 or other protrusion for placement of the hub or battery.

Figure 23:
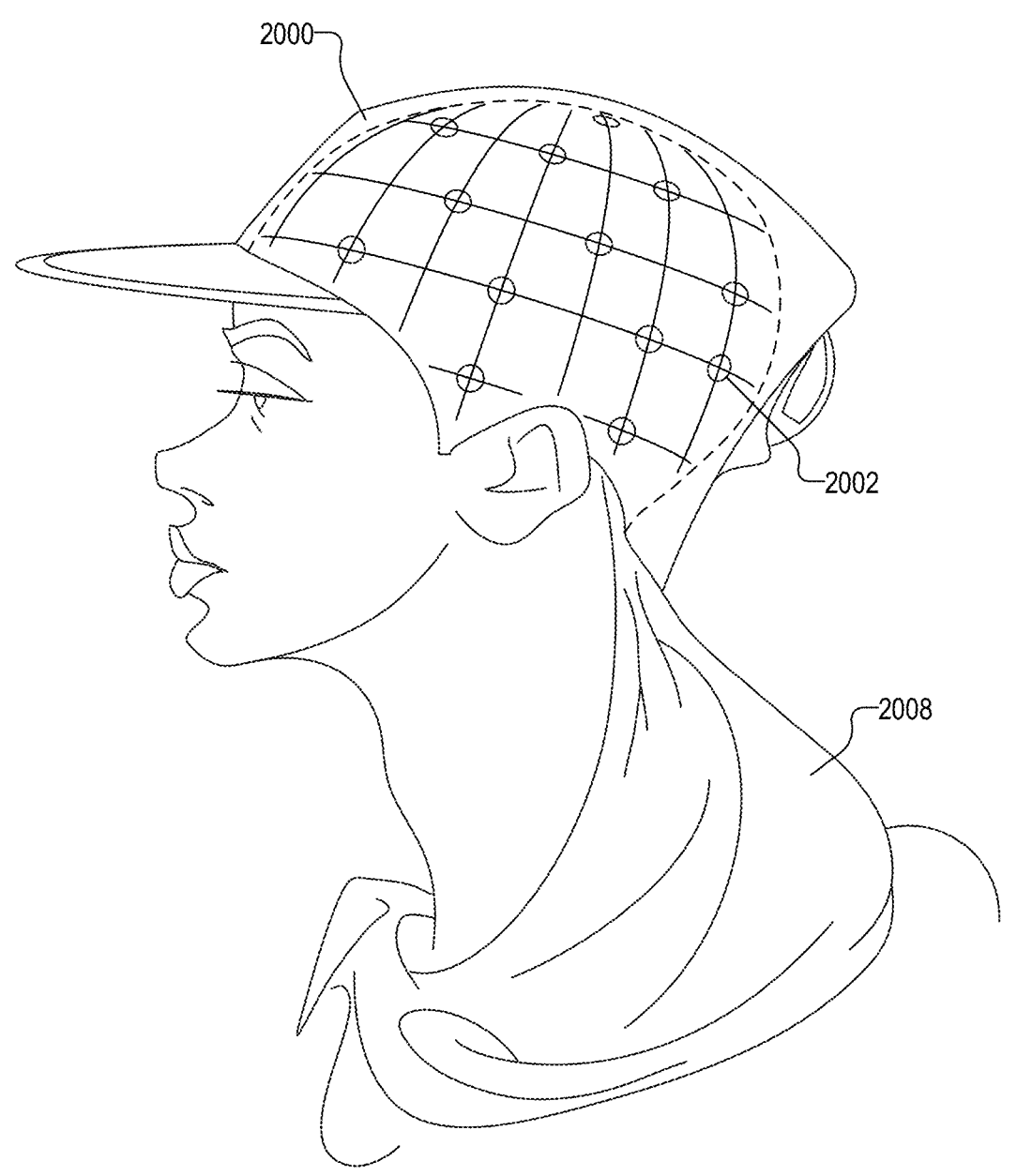
Figure 24:
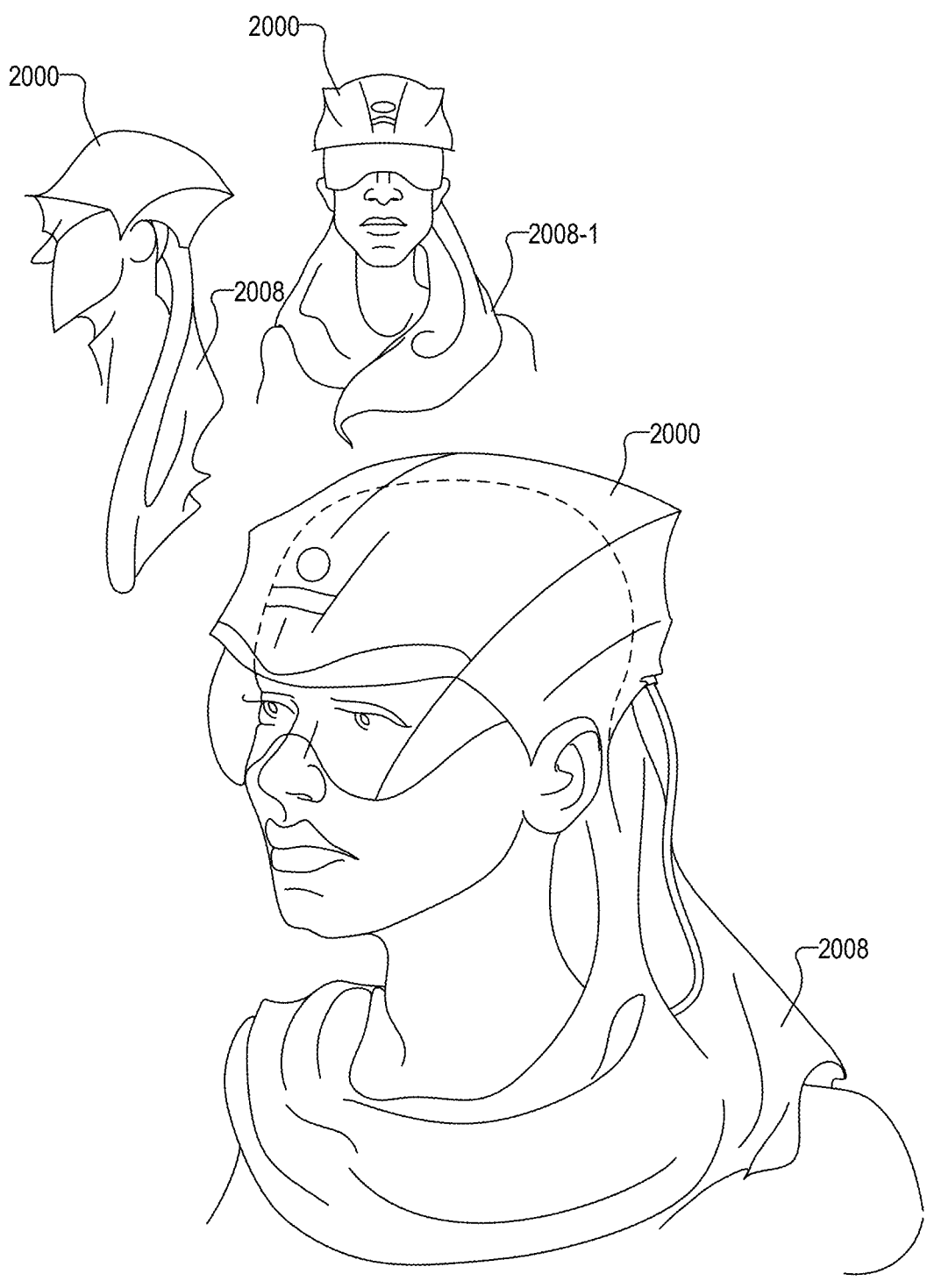
Figure 25:
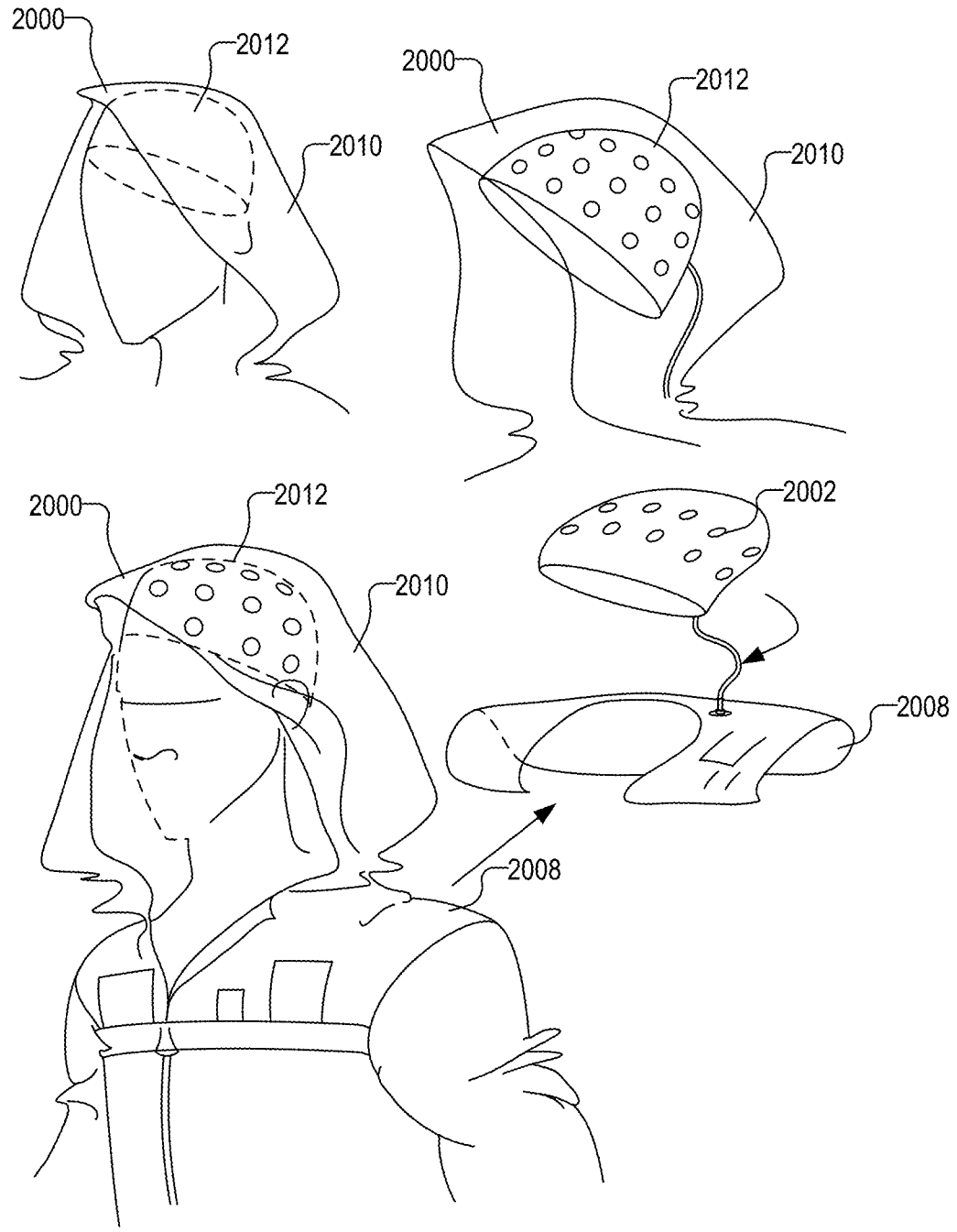

FIG. 23 illustrates another embodiment of a wearable device 2000 in the form of a cap with a wearable garment 2008 in the form of a scarf that may contain or conceal a cable, battery, and/or hub. FIG. 24 illustrates additional embodiments of a wearable device 2000 in the form of a helmet with a one-piece scarf 2008 or two-piece scarf 2008-1. FIG. 25 illustrates an embodiment of a wearable device 2000 that includes a hood 2010 and a beanie 2012 which contains the modules 2002, as well as a wearable garment 2008 that may contain a battery or hub.

FIG. 26 illustrates an exemplary method 2600. While FIG. 26 illustrates exemplary operations according to one embodiment, other embodiments may omit, add to, reorder, and/or modify any of the operations shown in FIG. 26. One or more of the operations shown in FIG. 26 may be performed by any system described herein (e.g., optical measurement system 100, brain interface system 500, or optical measurement system 1200), any components included therein (e.g., wearable module 600), and/or any implementation thereof.

In operation 2602, a light guide included in a wearable module being worn by a user receives at least one light pulse emitted by a light source. Operation 2602 may be performed in any of the ways described herein.

In operation 2604, the light guide guides signal photons included in the at least one light pulse toward a target within a body of the user. Operation 2604 may be performed in any of the ways described herein.

In operation 2606, the optical member directs the first light pulse and the second light pulse to a proximal end of a light guide included in the wearable module. Operation 2606 may be performed in any of the ways described herein.

In operation 2608, a light diverter included in the wearable module diverts reference photons included in the light pulse toward at least one detector configured to detect the reference photons. Operation 2608 may be performed in any of the ways described herein.

Figure 27:
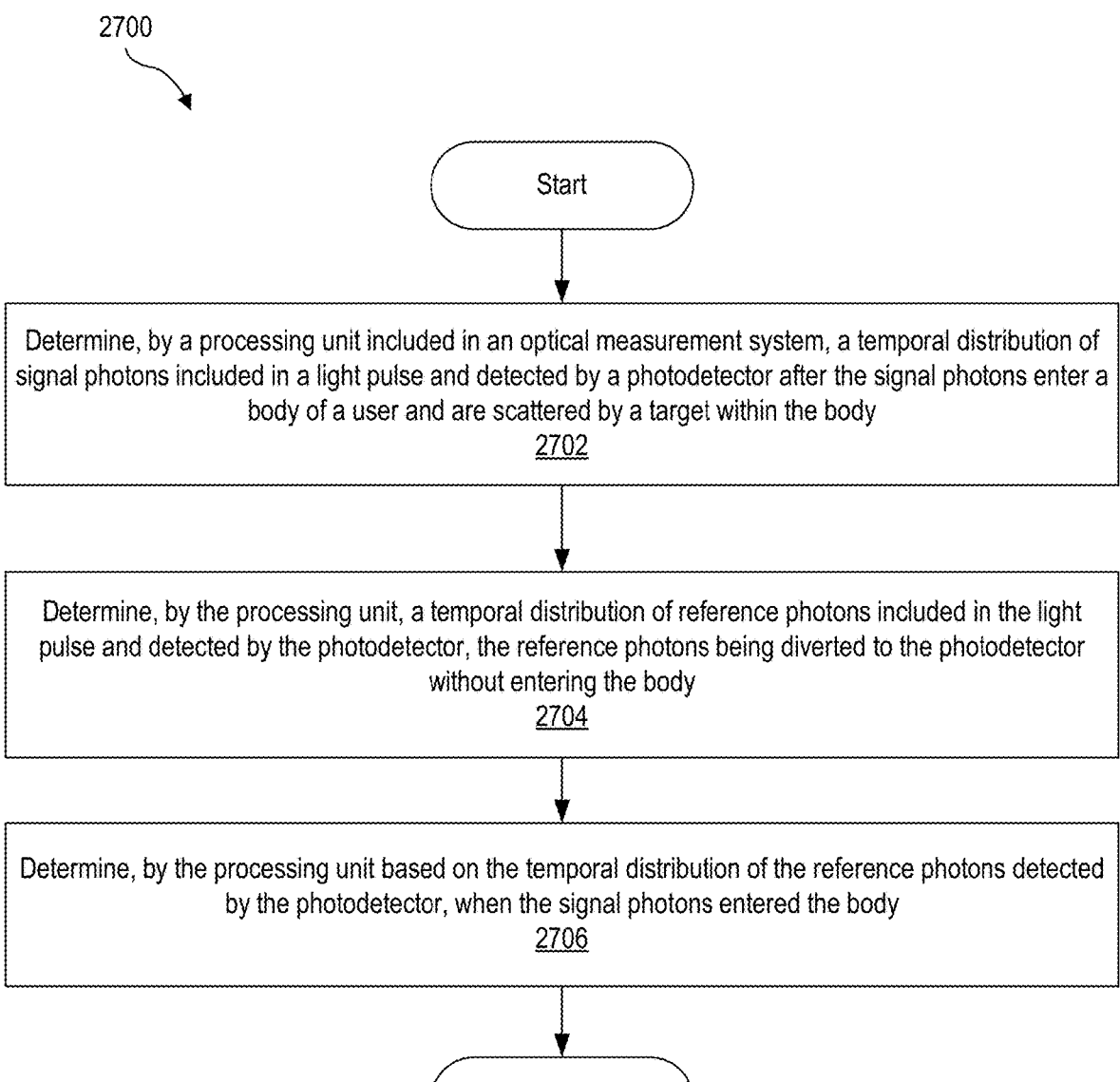

FIG. 27 illustrates an exemplary method 2700. While FIG. 27 illustrates exemplary operations according to one embodiment, other embodiments may omit, add to, reorder, and/or modify any of the operations shown in FIG. 27. One or more of the operations shown in FIG. 27 may be performed by any system described herein (e.g., optical measurement system 100, brain interface system 500, or optical measurement system 1200), any components included therein (e.g., wearable module 600), and/or any implementation thereof.

In operation 2702, a processing unit included in an optical measurement system determines a temporal distribution of signal photons included in a light pulse and detected by a detector after the signal photons enter a body of a user and are scattered by a target within the body. Operation 2702 may be performed in any of the ways described herein.

In operation 2704, the processing unit determines a temporal distribution of reference photons included in the light pulse and detected by the detector, the reference photons being diverted to the detector without entering the body. Operation 2704 may be performed in any of the ways described herein.

In operation 2706, the processing unit determines, based on the temporal distribution of the reference photons detected by the detector, when the signal photons entered the body. Operation 2706 may be performed in any of the ways described herein.

The systems, apparatuses, and methods described herein may determine absolute measures of [HbO2], [HHb], and [oxCCO] as well changes in the concentrations of these chromophores, thereby giving a full picture of oxidative metabolism and, thus, tissue function. Moreover, the systems, apparatuses, and methods described herein may also measure, based on changes in [HbO2] and [HHb], neural activity simultaneously with measuring the oxidative metabolism of the tissue. In some examples, the systems, apparatuses, and methods described herein may also measure neural activity based on one or more other modalities, such as EEG recordings and/or MEG. Additionally, the systems, apparatuses, and methods described herein may measure absolute optical properties of the tissue and neural activity in a wearable, whole-head coverage format, thereby measuring brain health and activity across the entire brain.

Regulation of tissue metabolite supply and cellular energy metabolism is critical to the central nervous system, where increased neuronal activity drives increased energy consumption and compensatory metabolic and vasculature changes. The systems described herein provide full-head coverage systems configured to fully characterize this process by measuring [HbO2], [HHb], [oxCCO], and neural firing in vivo. Such systems can help build models for neurovascular and neurometabolic coupling, which currently are not well-understood.

Additionally, the systems described herein provide a set of simultaneously-captured features that can enhance statistical models for brain activity decoding and biomarker exploration for brain state and neurodegenerative disorders. For example, in Alzheimer's disease, regional hypometabolism in the brain is a predictor for progressive cognitive decline and reduced cerebral metabolism is associated with carriers of Alzheimer's disease risk. Having a full picture of oxidative metabolism and neural activity can also help identify brain trauma and the progression of recovery. In the realm of neurovascular coupling, a rich data set capturing [HbO2], [HHb], [oxCCO], and neural firing in vivo can generate a model that accurately describes the correlation between blood flow and neural firing, which model can be highly advantageous in predicting changes in brain state and cognition.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 28:
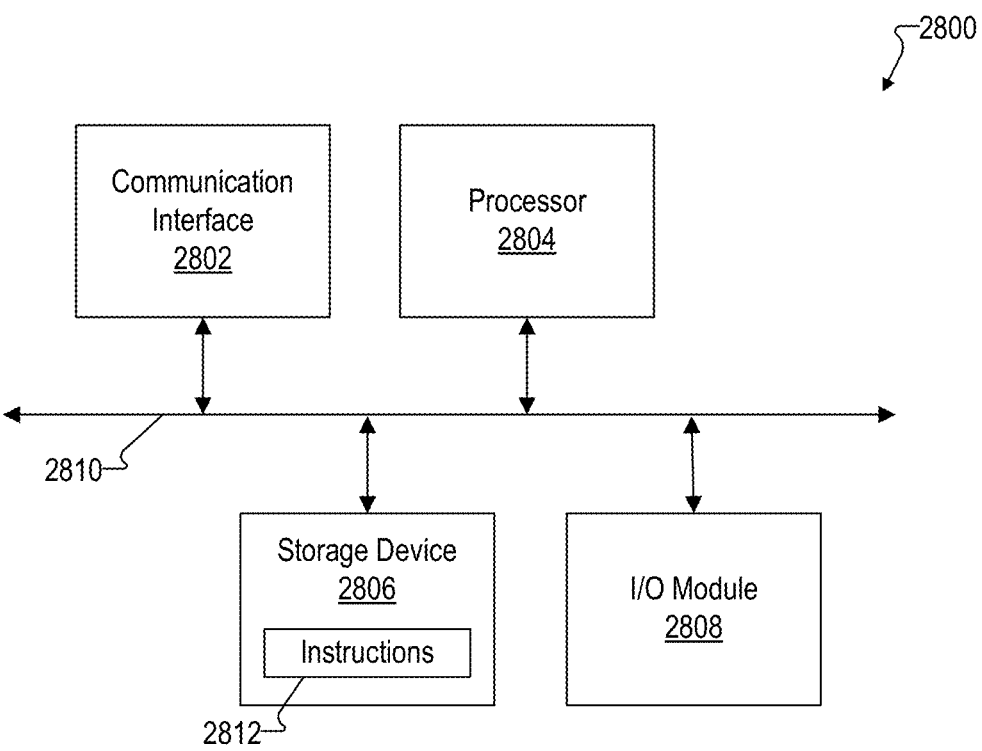
FIG. 28 illustrates an exemplary computing device.

FIG. 28 illustrates an exemplary computing device 2800 that may be specifically configured to perform one or more of the processes described herein. Any of the systems, units, computing devices, and/or other components described herein may be implemented by computing device 2800.

As shown in FIG. 28, computing device 2800 may include a communication interface 2802, a processor 2804, a storage device 2806, and an input/output ("I/O") module 2808 communicatively connected one to another via a communication infrastructure 2810. While an exemplary computing device 2800 is shown in FIG. 28, the components illustrated in FIG. 28 are not intended to be limiting. Additional or alternative components may be used in other embodiments. Components of computing device 2800 shown in FIG. 28 will now be described in additional detail.

Communication interface 2802 may be configured to communicate with one or more computing devices. Examples of communication interface 2802 include, without limitation, a wired network interface (such as a network interface card), a wireless network interface (such as a wireless network interface card), a modem, an audio/video connection, and any other suitable interface.

Processor 2804 generally represents any type or form of processing unit capable of processing data and/or interpreting, executing, and/or directing execution of one or more of the instructions, processes, and/or operations described herein. Processor 2804 may perform operations by executing computer-executable instructions 2812 (e.g., an application, software, code, and/or other executable data instance) stored in storage device 2806.

Storage device 2806 may include one or more data storage media, devices, or configurations and may employ any type, form, and combination of data storage media and/or device. For example, storage device 2806 may include, but is not limited to, any combination of the non-volatile media and/or volatile media described herein. Electronic data, including data described herein, may be temporarily and/or permanently stored in storage device 2806. For example, data representative of computer-executable instructions 2812 configured to direct processor 2804 to perform any of the operations described herein may be stored within storage device 2806. In some examples, data may be arranged in one or more databases residing within storage device 2806.

I/O module 2808 may include one or more I/O modules configured to receive user input and provide user output. I/O module 2808 may include any hardware, firmware, software, or combination thereof supportive of input and output capabilities. For example, I/O module 2808 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 2808 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 2808 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An optical measurement system comprising:
a detector configured to detect:
signal photons included in a light pulse after the signal photons enter a body of a user and are scattered by a target within the body, and
reference photons included in the light pulse, the reference photons being diverted to the detector without entering the body; and
a processing unit configured to:
determine a temporal distribution of the signal photons detected by the detector,
determine a temporal distribution of the reference photons detected by the detector, and
generate measurement data based on the temporal distribution of the signal photons and the temporal distribution of the reference photons.

2. The optical measurement system of claim 1, wherein the processing unit is further configured to determine, based on the measurement data, when the signal photons entered the body.

3. The optical measurement system of claim 1, wherein the measurement data comprises a histogram.

4. The optical measurement system of claim 1, wherein the processing unit is further configured to determine, based on the measurement data, at least one of an absolute value of a reduced scattering coefficient $\mu s$' of the target and an absolute value of an absorption coefficient $\mu a$ of the target.

5. The optical measurement system of claim 1, wherein the processing unit is further configured to determine, based on the measurement data, an absolute optical pathlength of the signal photons through the body.

6. The optical measurement system of claim 1, wherein the processing unit is further configured to determine, based on the measurement data, an oxidation state of cytochrome-c-oxidase present in the target.

7. The optical measurement system of claim 1, further comprising a wearable module, the wearable module comprising:
a light guide configured to receive the light pulse emitted by a light source and guide the signal photons included in the light pulse toward the body;
a light diverter configured to divert the reference photons included in the light pulse to the detector; and
a housing that houses both the light diverter and at least a portion of the light guide.

8. The optical measurement system of claim 7, wherein the processing unit is housed in the housing.

9. The optical measurement system of claim 7, further comprising an additional housing separate from the housing, wherein the processing unit is housed in the additional housing and communicatively coupled with the detector by way of a wired or wireless communication link.

10. The optical measurement system of claim 9, wherein the additional housing is wearable by the user.

11. The optical measurement system of claim 7, further comprising a head-mountable component configured to be worn on a head of the user,
wherein the wearable module is included in the head-mountable component.

12. The optical measurement system of claim 11, wherein the head-mountable component comprises a plurality of wearable modules.

13. The optical measurement system of claim 7, wherein the wearable module further comprises the detector.

14. The optical measurement system of claim 13, wherein the detector comprises a plurality of single-photon avalanche diode (SPAD) circuits.

15. The optical measurement system of claim 7, wherein the wearable module further comprises the light source.

16. The optical measurement system of claim 1, wherein the target comprises a brain of the user.

17. A method comprising:
determining, by a processing unit included in an optical measurement system, a temporal distribution of signal photons included in a light pulse and detected by a detector after the signal photons enter a body of a user and are scattered by a target within the body;
determining, by the processing unit, a temporal distribution of reference photons included in the light pulse and detected by the detector, the reference photons being diverted to the detector without entering the body; and
generating measurement data based on the temporal distribution of the signal photons and the temporal distribution of the reference photons.

18. The method of claim 17, further comprising:
determining, by the processing unit based on the measurement data, when the signal photons entered the body.

19. The method of claim 17, further comprising:
determining, by the processing unit based on the measurement data, one or more of an absolute value of a reduced scattering coefficient $\mu s$' of the target or an absolute value of an absorption coefficient $\mu a$ of the target.

20. The method of claim 17, further comprising:
determining, by the processing unit based on the measurement data, an absolute optical pathlength of the signal photons through the body.

21. The method of claim 17, further comprising:
determining, by the processing unit based on the measurement data, an oxidation state of cytochrome-c-oxidase present in the target.

* * * * *